(12) United States Patent
Verdin et al.

(10) Patent No.: US 7,273,713 B2
(45) Date of Patent: Sep. 25, 2007

(54) METHODS OF MODULATING MITOCHONDRIAL NAD-DEPENDENT DEACETYLASE

(75) Inventors: Eric M. Verdin, San Francisco, CA (US); Brian J. North, San Francisco, CA (US); Bjoern Schwer, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 453 days.

(21) Appl. No.: 10/444,633

(22) Filed: May 22, 2003

(65) Prior Publication Data

US 2004/0091953 A1 May 13, 2004

Related U.S. Application Data

(60) Provisional application No. 60/383,069, filed on May 23, 2002.

(51) Int. Cl.
*G01N 33/53* (2006.01)
(52) U.S. Cl. .................. 435/7.6; 435/7.72; 435/18
(58) Field of Classification Search ................ 435/7.6, 435/7.72, 18
See application file for complete search history.

(56) References Cited

U.S. PATENT DOCUMENTS

2002/0120008 A1 8/2002 Benzer et al.
2003/0082668 A1 5/2003 Tamal et al.

FOREIGN PATENT DOCUMENTS

| WO | WO 01/40506 | 6/2001 |
|----|-------------|--------|
| WO | WO 02/102981 | 12/2002 |
| WO | WO 03-004621 | 1/2003 |
| WO | WO 03/099210 | 12/2003 |
| WO | WO 2004/065169 | 7/2004 |

OTHER PUBLICATIONS

Frye, RA (1999) Characterization of five human cDNAs with homology to the yeast SIR2 gene: Sir2-like proteins (Sirtuins) metabolize NAD and may have protein ADP-Ribosyltransferase activity. Biochemical and Biophysical Res Comm 260: 273-9.*
Product Information: Histone from calf thymus Product No. H4380. Sigma online catalog, www.sigma-aldrich.com, 2006.*
Ait-Si-Ali S, Ramirez S, Robin P, Trouche D, and Harel-Bellan A (1998) A rapid and sensitive assay for histone acetyl-transferase activity. Nucleic Acids Research 26: pp. 3869-3870.*
Imai S, Armstrong CM, Kaeberlein M, and Guarente L (2000) Transcriptional silencing and longevity protein Sir2 is an NAD-dependent histone deacetylase. Nature 403: pp. 795-800.*
Product Information: Histone from calf thymus Product No. H4380. Sigma online catalog, www.sigma-aldrich.com.*
White DA, Belyaev ND, Turner BM (1999) Preparation of site-specific antibodies to acetylated histones. Methods 19: pp. 417-424.*
Landry J et al (May 23, 2000) The silencing protein SIR2 and its homologs are NAD-dependent protein deacetylases. Proc Natl Acad Sci, vol. 7, No. 11, pp. 5807-5811.*
Sherman JM et al (Sep. 1999) The conserved core of a human SIR2 homologue functions in yeast silencing. Mol Biol Cell, vol. 10, pp. 3045-3059.*
Moazed D (published online Mar. 7, 2001) Enzymatic activities of Sir2 and chromatin silencing. Curr Opin Cell Biol, vol. 13, pp. 232-238.*
Haigis MC et al (Sep. 8, 2006) SIRT4 inhibits glutamate dehydrogenase and opposes the effects of calorie restriction in pancreatic beta cells. Cell, vol. 126, pp. 941-954.*
Yang et al. (2000) *Genomics* 69:355-369.
Frye (2000) *Biochem. Biophys. Res. Comm.* 273:793-798.
GenBank Accession Nos. NM_012239 and AF083109.
Frye, Roy A., "Characterization of five human cDNAs with Homology to the Yeast SIR2 Gene: Sir2-like Proteins (Sirtuins) Metabolize NAD and May Have Protein ADP-Ribosyltransferase Activity", Biochemical and Biophysical Research Communications, vol. 260, No. 1, (1999), pp. 273-279.
Grozinger et al., "Identification of a Class of Small Molecule Inhibitors of the Sirtuin Family of NAD-dependent Deacetylases by Phenotypic Screening", The Journal of Biological Chemistry, vol. 276, No. 42, (2001), pp. 38837-38843.
Landry et al., "Role of NAD+ in the Deacetylase Activity of the SIR2-like Proteins", Biochemical and Biophysical Research Communications, vol. 278, No. 3, (2000), pp. 685-690.
Onyango et al., "SIRT3, a human SIR2 homologue, is an NAD-dependent deacetylase localized to mitochondria", Proceedings of the National Academy of Sciences, vol. 99, No. 21, (2002), pp. 13653-13658.
Schwer et al., The human silent information regulator (Sir)2 homologue hSIRT3 is a mitochoncrial nicotinamide adenine dinucleotide-dependent deacetylase, Journal of Cell Biology, vol. 158, No. 4, (2002), pp. 647-657.

* cited by examiner

*Primary Examiner*—Jon Weber
*Assistant Examiner*—Clark D Petersen
(74) *Attorney, Agent, or Firm*—Paula A. Borden; Bozicevic, Field & Francis LLP

(57) ABSTRACT

The present invention provides methods for identifying agents that modulate a level or an activity of a mitochondrial NAD-dependent deacetylase polypeptide, as well as agents identified by the methods. The invention further provides methods of modulating mitochondrial NAD-dependent deacetylase activity in a cell. The invention further provides methods of modulating mitochondrial function by modulating the activity of mitochondrial NAD-dependent deacetylase.

12 Claims, 9 Drawing Sheets

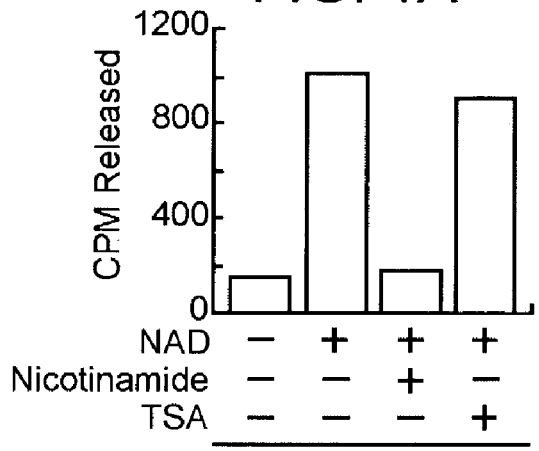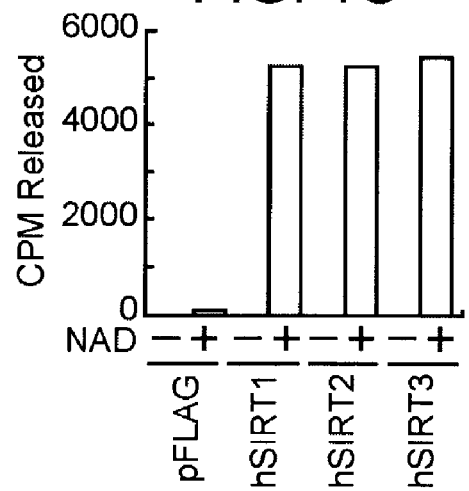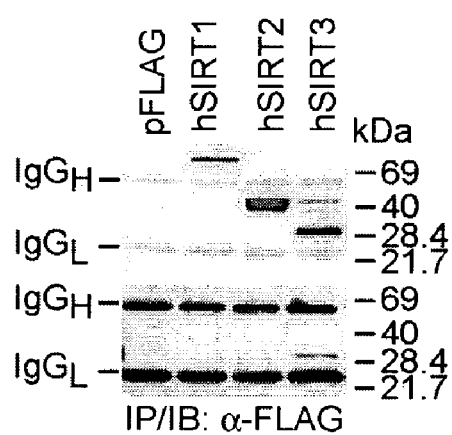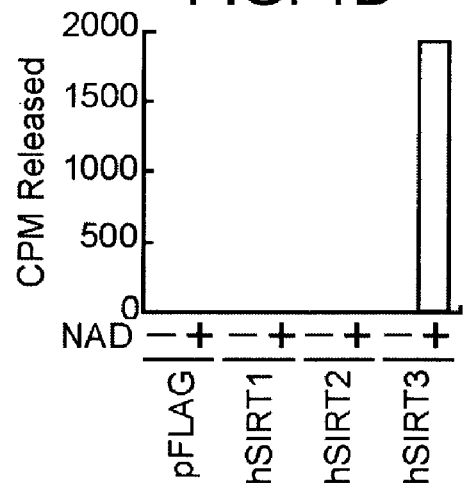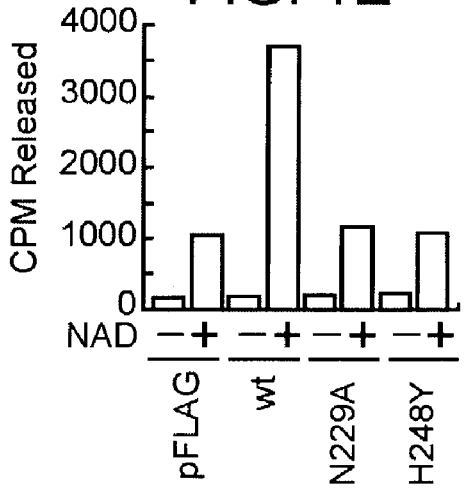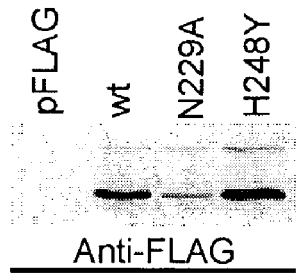

FIG. 7

MAFWGWRAAA ALRLWGRVVE RVEAGGGVGP FQACGCRLVL
GGRDDVSAGL RGSHGARGEP LDPARPLQRP PRPEVPRAFR RQPRAAAPSF
FFSSIKGGRR SISFSVGASS VVGSGGSSDK GKLSLQDVAE LIRARACQRV
VVMVGAGIST PSGIPDFRSP GSGLYSNLQQ YDLPYPEAIF ELPFFFHNPK
PFFTLAKELY PGNYKPNVTH YFLRLLHDKG LLLRLYTQNI DGLERVSGIP
ASKLVEAHGT FASATCTVCQ RPFPGEDIRA DVMADRVPRC
PVCTGVVKPD IVFFGEPLPQ RFLLHVVDFP MADLLLILGT SLEVEPFASL
TEAVRSSVPR LLINRDLVGP LAWHPRSRDV AQLGDVVHGV
ESLVELLGWT EEMRDLVQRE TGKLDGPDK (SEQ ID NO:01)

SEQUENCE LISTING

```
<160> NUMBER OF SEQ ID NOS: 8

<210> SEQ ID NO 1
<211> LENGTH: 399
<212> TYPE: PRT
<213> ORGANISM: H. sapiens

<400> SEQUENCE: 1

Met Ala Phe Trp Gly Trp Arg Ala Ala Ala Leu Arg Leu Trp Gly
1               5                   10                  15

Arg Val Val Glu Arg Val Glu Ala Gly Gly Val Gly Pro Phe Gln
                20                  25                  30

Ala Cys Gly Cys Arg Leu Val Leu Gly Gly Arg Asp Asp Val Ser Ala
            35                  40                  45

Gly Leu Arg Gly Ser His Gly Ala Arg Gly Glu Pro Leu Asp Pro Ala
    50                  55                  60

Arg Pro Leu Gln Arg Pro Pro Arg Pro Glu Val Pro Arg Ala Phe Arg
65                  70                  75                  80

Arg Gln Pro Arg Ala Ala Ala Pro Ser Phe Phe Phe Ser Ser Ile Lys
                85                  90                  95

Gly Gly Arg Arg Ser Ile Ser Phe Ser Val Gly Ala Ser Ser Val Val
                100                 105                 110

Gly Ser Gly Gly Ser Ser Asp Lys Gly Lys Leu Ser Leu Gln Asp Val
            115                 120                 125

Ala Glu Leu Ile Arg Ala Arg Ala Cys Gln Arg Val Val Val Met Val
    130                 135                 140

Gly Ala Gly Ile Ser Thr Pro Ser Gly Ile Pro Asp Phe Arg Ser Pro
145                 150                 155                 160

Gly Ser Gly Leu Tyr Ser Asn Leu Gln Gln Tyr Asp Leu Pro Tyr Pro
                165                 170                 175

Glu Ala Ile Phe Glu Leu Pro Phe Phe His Asn Pro Lys Pro Phe
                180                 185                 190

Phe Thr Leu Ala Lys Glu Leu Tyr Pro Gly Asn Tyr Lys Pro Asn Val
            195                 200                 205

Thr His Tyr Phe Leu Arg Leu Leu His Asp Lys Gly Leu Leu Leu Arg
        210                 215                 220
```

-continued

```
Leu Tyr Thr Gln Asn Ile Asp Gly Leu Glu Arg Val Ser Gly Ile Pro
225                 230                 235                 240

Ala Ser Lys Leu Val Glu Ala His Gly Thr Phe Ala Ser Ala Thr Cys
                245                 250                 255

Thr Val Cys Gln Arg Pro Phe Pro Gly Glu Asp Ile Arg Ala Asp Val
            260                 265                 270

Met Ala Asp Arg Val Pro Arg Cys Pro Val Cys Thr Gly Val Val Lys
        275                 280                 285

Pro Asp Ile Val Phe Phe Gly Glu Pro Leu Pro Gln Arg Phe Leu Leu
    290                 295                 300

His Val Val Asp Phe Pro Met Ala Asp Leu Leu Ile Leu Gly Thr
305                 310                 315                 320

Ser Leu Glu Val Glu Pro Phe Ala Ser Leu Thr Glu Ala Val Arg Ser
                325                 330                 335

Ser Val Pro Arg Leu Leu Ile Asn Arg Asp Leu Val Gly Pro Leu Ala
            340                 345                 350

Trp His Pro Arg Ser Arg Asp Val Ala Gln Leu Gly Asp Val His
        355                 360                 365

Gly Val Glu Ser Leu Val Glu Leu Leu Gly Trp Thr Glu Glu Met Arg
    370                 375                 380

Asp Leu Val Gln Arg Glu Thr Gly Lys Leu Asp Gly Pro Asp Lys
385                 390                 395
```

```
<210> SEQ ID NO 2
<211> LENGTH: 22
<212> TYPE: PRT
<213> ORGANISM: Artificial Sequence
<220> FEATURE:
<223> OTHER INFORMATION: fragment of histone 4
<220> FEATURE:
<221> NAME/KEY: ACETYLATION
<222> LOCATION: (6)...(6)
<223> OTHER INFORMATION: Xaa = acetylated lysine
<220> FEATURE:
<221> NAME/KEY: ACETYLATION
<222> LOCATION: (9)...(9)
<223> OTHER INFORMATION: Xaa = acetylated lysine
<220> FEATURE:
<221> NAME/KEY: ACETYLATION
<222> LOCATION: (13)...(13)
<223> OTHER INFORMATION: Xaa = acetylated lysine
<220> FEATURE:
<221> NAME/KEY: ACETYLATION
<222> LOCATION: (17)...(17)
<223> OTHER INFORMATION: Xaa = acetylated lysine

<400> SEQUENCE: 2

Met Ser Gly Arg Gly Xaa Gly Gly Xaa Gly Leu Gly Xaa Gly Gly Ala
  1               5                  10                  15

Xaa Arg His Arg Lys Val
            20
```

```
<210> SEQ ID NO 3
<211> LENGTH: 30
<212> TYPE: PRT
<213> ORGANISM: Artificial Sequence
<220> FEATURE:
<223> OTHER INFORMATION: fragment of histone 4
<220> FEATURE:
<221> NAME/KEY: ACETYLATION
<222> LOCATION: (6)...(6)
<223> OTHER INFORMATION: Xaa = acetylated lysine
<220> FEATURE:
<221> NAME/KEY: ACETYLATION
```

```
<222> LOCATION: (9)...(9)
<223> OTHER INFORMATION: Xaa = acetylated lysine
<220> FEATURE:
<221> NAME/KEY: ACETYLATION
<222> LOCATION: (13)...(13)
<223> OTHER INFORMATION: Xaa = acetylated lysine
<220> FEATURE:
<221> NAME/KEY: ACETYLATION
<222> LOCATION: (17)...(17)
<223> OTHER INFORMATION: Xaa = acetylated lysine

<400> SEQUENCE: 3

Met Ser Gly Arg Gly Xaa Gly Gly Xaa Gly Leu Gly Xaa Gly Gly Ala
1               5                   10                  15

Xaa Arg His Arg Lys Val Leu Arg Asp Asn Ile Gln Gly Ile
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: fragment of histone 3
<220> FEATURE:
<221> NAME/KEY: ACETYLATION
<222> LOCATION: (5)...(5)
<223> OTHER INFORMATION: Xaa = acetylated lysine
<220> FEATURE:
<221> NAME/KEY: ACETYLATION
<222> LOCATION: (10)...(10)
<223> OTHER INFORMATION: Xaa = acetylated lysine
<220> FEATURE:
<221> NAME/KEY: ACETYLATION
<222> LOCATION: (15)...(15)
<223> OTHER INFORMATION: Xaa = acetylated lysine
<220> FEATURE:
<221> NAME/KEY: ACETYLATION
<222> LOCATION: (19)...(19)
<223> OTHER INFORMATION: Xaa = acetylated lysine

<400> SEQUENCE: 4

Met Ala Arg Thr Xaa Gln Thr Ala Arg Xaa Ser Thr Gly Gly Xaa Ala
1               5                   10                  15

Pro Arg Xaa Gln Leu Ala Thr Lys Ala Ala Arg Lys Ser Ala
            20                  25                  30

<210> SEQ ID NO 5
<211> LENGTH: 15
<212> TYPE: PRT
<213> ORGANISM: Artificial Sequence
<220> FEATURE:
<223> OTHER INFORMATION: fragment of hSIRT3

<400> SEQUENCE: 5

Asp Leu Val Gln Arg Glu Thr Gly Lys Leu Asp Gly Pro Asp Lys
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: fragment of hSIRT3

<400> SEQUENCE: 6

Asp Leu Val Gln Arg Glu Thr Gly Lys Leu Asp Gly Pro Asp Lys
1               5                   10                  15

<210> SEQ ID NO 7
```

```
<211> LENGTH: 28
<212> TYPE: DNA
<213> ORGANISM: Artificial Sequence
<220> FEATURE:
<223> OTHER INFORMATION: primer

<400> SEQUENCE: 7
gtgaattcat atcttttct gtgggtgc                                    28

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
gtgaattcgc ccttgaatca tc                                         22
```

US 7,273,713 B2

METHODS OF MODULATING MITOCHONDRIAL NAD-DEPENDENT DEACETYLASE

FIELD OF THE INVENTION

The present invention is in the field of deacetylase enzymes.

BACKGROUND OF THE INVENTION

Silent Information Regulator 2 (Sir2) protein is involved in transcriptional silencing and DNA damage repair in yeast. It also increases life span in yeast and in *Caenorhabditis elegans*. Yeast Sir2 protein has an NAD-dependent histone deacetylase activity that links Sir2 functions to cellular metabolism. This NAD-dependent deacetylase activity is conserved from bacteria to humans and mammalian Sir2 homologues also have NAD-dependent histone deacetylase activity. The NAD-dependency of Sir2-like enzymes distinguishes them from the class I and II HDAC histone deacetylases that use a zinc-catalyzed mechanism. Seven Sir2 homologues have been identified in humans and are designated hSIRT1-7. Among the human homologues, hSIRT1, hSIRT2 and hSIRT3 the most homologous to yeast Sir2 and have NAD-dependent deacetylase activity. At present, very little is known about the in vivo functions of mammalian SIR2 homologues. hSIRT1 deacetylates the transcription factor p53 thereby inhibiting p53 activation and apoptosis in response to DNA damage and oxidative stress.

Literature

Yang et al. (2000) *Genomics* 69:355-369; Frye (2000) *Biochem. Biophys. Res. Comm.* 273:793-798; GenBank Accession Nos. NM_012239 and AF083109.

SUMMARY OF THE INVENTION

The present invention provides methods for identifying agents that modulate a level or an activity of a mitochondrial NAD-dependent deacetylase polypeptide, as well as agents identified by the methods. The invention further provides methods of modulating mitochondrial NAD-dependent deacetylase activity in a cell. The invention further provides methods of modulating mitochondrial function by modulating the activity of mitochondrial NAD-dependent deacetylase.

Features of the Invention

The present invention features an in vitro method of identifying an agent that modulates an enzymatic activity of a human mitochondrial NAD-dependent deacetylase. The method generally involves contacting a mitochondrial NAD-dependent deacetylase polypeptide with a test agent in an assay mixture that comprises nicotinamide adenine dinucleotide (NAD) and an acetylated histone peptide; and determining the effect, if any, of the test agent on the enzymatic activity of mitochondrial NAD-dependent deacetylase. In some embodiments, the human mitochondrial NAD-dependent deacetylase polypeptide comprises an amino acid sequence as set forth in SEQ ID NO:01. In some embodiments, the acetylated histone peptide comprises amino acids 1-22 of histone 4. In some embodiments, the acetylated histone peptide contains a $^{14}C$-labeled acetyl group, and determining the effect of the agent on the enzymatic activity of the deacetylase is performed by measuring release of the radioactive acetyl group. In other embodiments, determining the effect of the agent on the enzymatic activity of the deacetylase is performed by detecting binding of an antibody specific for acetylated histone.

The present invention further features an in vitro method for identifying an agent that modulates a level of mitochondrial NAD-dependent deacetylase in a cell. The method generally involves contacting a cell that produces mitochondrial NAD-dependent deacetylase with a test agent; and determining the effect, if any, of the test agent on the level of mitochondrial NAD-dependent deacetylase. In some embodiments, determining the effect of the agent on the level of the deacetylase is performed by determining a level of mitochondrial NAD-dependent deacetylase mRNA in the cell. In other embodiments, determining the effect of the agent on the level of the deacetylase is performed by determining a level of mitochondrial NAD-dependent deacetylase polypeptide in the cell.

The present invention further features a biologically active agent identified by a screening method according to the invention. The invention further features a pharmaceutical composition comprising a biologically active agent that reduces a level or an activity of a mitochondrial NAD-dependent deacetylase protein; and a pharmaceutically acceptable excipient.

BRIEF DESCRIPTION OF THE DRAWINGS

FIGS. 1A-F depict deacetylase activity in mitochondria.

FIG. 7 depicts the amino acid sequence of human SIRT3 (SEQ ID NO:01).

DEFINITIONS

Figure 2C:
FIGS. 2A-C depict localization of deacetylase activity in mitochondria.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

A "substantially isolated" or "isolated" polypeptide is one that is substantially free of the macromolecules with which it is associated in nature. By substantially free is meant at least 50%, preferably at least 70%, more preferably at least 80%, and even more preferably at least 90% free of the materials with which it is associated in nature.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

The term "disorder associated with mitochondrial malfunction," as used herein, refers to any disorder that is directly or indirectly a result of, or caused by, malfunction of a mitochondrion in a cell.

The terms "cancer", "neoplasm", "tumor", and "carcinoma", are used interchangeably herein to refer to cells which exhibit relatively autonomous growth, so that they exhibit an aberrant growth phenotype characterized by a significant loss of control of cell proliferation. Cancerous cells can be benign or malignant.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a mitochondrial NAD-dependent deacetylase" includes a plurality of such deacetylases and reference to "the agent" includes reference to one or more agents and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The instant invention provides methods for identifying agents that modulate an enzymatic activity of a mitochondrial NAD-dependent deacetylase. The invention further provides agents identified by the instant methods, as well as methods of modulating the activity of the mitochondrial NAD-dependent deacetylase. Agents that modulate the activity of an NAD-dependent mitochondrial deacetylase are useful to ameliorate disorders associated with mitochondrial malfunction.

The instant invention is based on the observation that human SIRT3 (hSIRT3) is a nuclear-encoded NAD-dependent deacetylase residing within the mitochondria. hSIRT3 is proteolytically cleaved by a mitochondrial enzyme to a catalytically active form of having a molecular weight of about 28 kDa. The identification of the activity of hSIRT3 allowed development of assays to identify agents that modulate the activity of this enzyme. Such agents are useful in treating disorders arising from mitochondrial malfunction.

Screening Methods

The invention provides in vitro methods of identifying an agent that modulates a level or an activity of a mitochondrial NAD-dependent deacetylase. The methods generally involve contacting a mitochondrial NAD-dependent deacetylase protein, or a cell that produces a mitochondrial NAD-dependent deacetylase protein, with a test agent, and determining the effect, if any, on a level or an activity of the mitochondrial NAD-dependent deacetylase protein.

In some embodiments, the methods are cell-free methods. Cell-free methods generally involve contacting a mitochondrial NAD-dependent deacetylase with a test agent and determining the effect, if any, of the test agent on the enzymatic activity of the mitochondrial NAD-dependent deacetylase.

In other embodiments, the methods are cell-based methods. Cell-based methods generally involve contacting a cell that produces mitochondrial NAD-dependent deacetylase with a test agent and determining the effect, if any, of the test agent on the level of mitochondrial NAD-dependent deacetylase mRNA or mitochondrial NAD-dependent deacetylase protein in the cell.

As used herein, the term "determining" refers to both quantitative and qualitative determinations and as such, the term "determining" is used interchangeably herein with "assaying," "measuring," and the like.

The term "mitochondrial NAD-dependent deacetylase polypeptide" encompasses human mitochondrial NAD-dependent deacetylase proteins (e.g., human SIRT3 proteins) having the amino acid sequences set forth in any of GenBank Accession Nos. NM_012239; and AF0831087, where the polypeptide is a nuclear-encoded, mitochondrial protein and exhibits NAD-dependent mitochondrial NAD-dependent deacetylase activity. The term comprises a mitochondrial NAD-dependent deacetylase polypeptide comprises the amino acid sequence as set forth in SEQ ID NO:01 and depicted in FIG. 7; catalytically active fragments thereof; and catalytically active variants thereof. Catalytically active fragments include fragments lacking from about 1 to about 120 N-terminal amino acids of the sequence set forth in SEQ ID NO:01. For example, catalytically active fragments lacking from about 1 to about 10, from about 10 to about 20, from about 20 to about 30, from about 30 to about 40, from about 40 to about 50, from about 50 to about 60, from about 60 to about 70, from about 70 to about 80, from about 80 to about 90, from about 90 to about 100, or from about 100 to about 120 N-terminal amino acids of the sequence set forth in SEQ ID NO:01 can be used in a subject method. The term encompasses an enzyme that is proteolytically processed in the mitochondria by a mitochondrial enzyme referred to as MPP, which cleaves the 44 kDa form of the enzyme to a catalytically active 28 kDa form. In many embodiments, the 28 kDa form is used in the instant methods. The term encompasses variants that have insertions, deletions, and/or conservative amino acid substitutions that do not affect the ability of the protein to deacetylate an appropriate substrate (e.g., acetylated histone 4, or an acetylated fragment thereof) in an NAD-dependent fashion. In some embodiments, the mitochondrial NAD-dependent deacetylase is recombinant, e.g., produced in a cell transfected with an expression construct comprising a nucleotide sequence that encodes the mitochondrial NAD-dependent deacetylase.

The term "mitochondrial NAD-dependent deacetylase polypeptide" further encompasses fusion proteins comprising a mitochondrial NAD-dependent deacetylase and a heterologous polypeptide ("fusion partners"), where suitable fusion partners include immunological tags such as epitope tags, including, but not limited to, hemagglutinin, FLAG, and the like; proteins that provide for a detectable signal, including, but not limited to, fluorescent proteins (e.g., a green fluorescent protein, a fluorescent protein from an Anthozoan species, and the like), enzymes (e.g., β-galactosidase, luciferase, horse radish peroxidase, etc.), and the like; polypeptides that facilitate purification or isolation of the fusion protein, e.g., metal ion binding polypeptides such as 6His tags (e.g., mitochondrial NAD-dependent deacetylase/6His), GST, and the like. The term "mitochondrial NAD-dependent deacetylase polypeptide" further includes a mitochondrial NAD-dependent deacetylase polypeptide modified to include one or more specific protease cleavage sites.

Where the assay is an in vitro cell-free assay, the methods generally involve contacting a mitochondrial NAD-dependent deacetylase polypeptide with a test agent. The mitochondrial NAD-dependent deacetylase polypeptide may be, but need not be, purified. For example, the mitochondrial NAD-dependent deacetylase polypeptide can be in a cell lysate, or may be isolated, or partially purified. Thus, the assay can be conducted in the presence of additional components, as long as the additional components do not adversely affect the reaction to an unacceptable degree.

Where the assay is an in vitro cell-based assay, any of a variety of cells can be used. The cells used in the assay are usually eukaryotic cells, including, but not limited to, rodent cells, human cells, and yeast cells. The cells may be primary cell cultures or may be immortalized cell lines. The cells may be "recombinant," e.g., the cell may have transiently or stably introduced therein a construct (e.g., a plasmid, a recombinant viral vector, or any other suitable vector) that comprises a nucleotide sequence encoding a mitochondrial NAD-dependent deacetylase polypeptide, or that comprises a nucleotide sequence that comprises a mitochondrial NAD-dependent deacetylase promoter operably linked to a reporter gene.

The terms "candidate agent," "test agent," "agent", "substance" and "compound" are used interchangeably herein. Candidate agents encompass numerous chemical classes, typically synthetic, semi-synthetic, or naturally occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.) and can also be used. Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of the invention include controls, where suitable controls include a sample (e.g., a sample comprising mitochondrial NAD-dependent deacetylase protein, or a cell that synthesizes mitochondrial NAD-dependent deacetylase) in the absence of the test agent. Generally a plurality of assay mixtures is run in parallel with different agent concentrations to obtain a differential response to the various concentrations. Typically, one of these concentrations serves as a negative control, i.e. at zero concentration or below the level of detection.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The components of the assay mixture are added in any order that provides for the requisite binding or other activity. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

The screening methods may be designed a number of different ways, where a variety of assay configurations and protocols may be employed, as are known in the art. For example, one of the components may be bound to a solid support, and the remaining components contacted with the support bound component. The above components of the method may be combined at substantially the same time or at different times.

Where the assay is a binding assay, following the contact and incubation steps, the subject methods will generally, though not necessarily, further include a washing step to remove unbound components, where such a washing step is generally employed when required to remove label that would give rise to a background signal during detection, such as radioactive or fluorescently labeled non-specifically bound components. Following the optional washing step, the presence of bound complexes will then be detected.

A test agent of interest is one that reduces a level of mitochondrial NAD-dependent deacetylase protein or inhibits a mitochondrial NAD-dependent deacetylase activity by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the test agent.

Methods of Detecting Agents that Modulate a Level of Mitochondrial NAD-Dependent Deacetylase mRNA and/or Mitochondrial NAD-Dependent Deacetylase Polypeptide The subject screening methods include methods of detecting an agent that modulates a level of a mitochondrial NAD-dependent deacetylase mRNA and/or mitochondrial NAD-dependent deacetylase polypeptide in a cell. In some embodiments, the methods involve contacting a cell that produces mitochondrial NAD-dependent deacetylase with a test agent, and determining the effect, if any, of the test agent on the level of mitochondrial NAD-dependent deacetylase mRNA in the cell.

A candidate agent is assessed for any cytotoxic activity it may exhibit toward the cell used in the assay, using well-known assays, such as trypan blue dye exclusion, an MTT (3-(4,5-dimethylthiazol-2-yl)-2,5-diphenyl-2H-tetrazolium bromide) assay, and the like. Agents that do not exhibit cytotoxic activity are considered candidate agents.

A wide variety of cell-based assays may be used for identifying agents which reduce a level of mitochondrial NAD-dependent deacetylase mRNA in a eukaryotic cell, using, for example, a cell that normally produces mitochondrial NAD-dependent deacetylase mRNA, a mammalian cell transformed with a construct comprising a mitochondrial NAD-dependent deacetylase-encoding cDNA such that the cDNA is overexpressed, or, alternatively, a construct comprising a mitochondrial NAD-dependent deacetylase promoter operably linked to a reporter gene.

Accordingly, the present invention provides a method for identifying an agent, particularly a biologically active agent, that reduces a level of mitochondrial NAD-dependent deacetylase expression in a cell, the method comprising: combining a candidate agent to be tested with a cell comprising a nucleic acid which encodes a mitochondrial NAD-dependent deacetylase polypeptide, or a construct comprising a mitochondrial NAD-dependent deacetylase promoter operably linked to a reporter gene; and determining the effect of said agent on mitochondrial NAD-dependent deacetylase expression. A decrease of at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, in the level (i.e., an amount) of mitochondrial NAD-dependent deacetylase mRNA and/or polypeptide following contacting the cell with a candidate agent being tested, compared to a control to which no agent is added, is an indication that the agent modulates mitochondrial NAD-dependent deacetylase expression.

Mitochondrial NAD-dependent deacetylase mRNA and/or polypeptide whose levels are being measured can be encoded by an endogenous mitochondrial NAD-dependent deacetylase polynucleotide, or the mitochondrial NAD-dependent deacetylase polynucleotide can be one that is comprised within a recombinant vector and introduced into the cell, i.e., the mitochondrial NAD-dependent deacetylase mRNA and/or polypeptide can be encoded by an exogenous mitochondrial NAD-dependent deacetylase polynucleotide. For example, a recombinant vector may comprise an isolated mitochondrial NAD-dependent deacetylase transcriptional regulatory sequence, such as a promoter sequence, operably linked to a reporter gene (e.g., β-galactosidase, chloramphenicol acetyl transferase, a fluorescent protein, luciferase, or other gene that can be easily assayed for expression).

In these embodiments, the method for identifying an agent that modulates a level of mitochondrial NAD-dependent deacetylase expression in a cell, comprises: combining a candidate agent to be tested with a cell comprising a nucleic acid which comprises a mitochondrial NAD-dependent deacetylase gene transcriptional regulatory element operably linked to a reporter gene; and determining the effect of said agent on reporter gene expression. A recombinant vector may comprise an isolated mitochondrial NAD-dependent deacetylase transcriptional regulatory sequence, such as a promoter sequence, operably linked to sequences coding for a mitochondrial NAD-dependent deacetylase polypeptide; or the transcriptional control sequences can be operably linked to coding sequences for a mitochondrial NAD-dependent deacetylase fusion protein comprising mitochondrial NAD-dependent deacetylase polypeptide fused to a polypeptide which facilitates detection. In these embodiments, the method comprises combining a candidate agent to be tested with a cell comprising a nucleic acid which comprises a mitochondrial NAD-dependent deacetylase gene transcriptional regulatory element operably linked to a mitochondrial NAD-dependent deacetylase polypeptide-coding sequence; and determining the effect of said agent on mitochondrial NAD-dependent deacetylase expression, which determination can be carried out by measuring an amount of mitochondrial NAD-dependent deacetylase mRNA, mitochondrial NAD-dependent deacetylase polypeptide, or mitochondrial NAD-dependent deacetylase fusion polypeptide produced by the cell.

Cell-based assays generally comprise the steps of contacting the cell with an agent to be tested, forming a test sample, and, after a suitable time, assessing the effect of the agent on mitochondrial NAD-dependent deacetylase expression. A control sample comprises the same cell without the candidate agent added. Mitochondrial NAD-dependent deacetylase expression levels are measured in both the test sample and the control sample. A comparison is made between mitochondrial NAD-dependent deacetylase expression level in the test sample and the control sample. Mitochondrial NAD-dependent deacetylase expression can be assessed using conventional assays. For example, when a mammalian cell line is transformed with a construct that results in expression of mitochondrial NAD-dependent deacetylase, mitochondrial NAD-dependent deacetylase mRNA levels can be detected and measured, or mitochondrial NAD-dependent deacetylase polypeptide levels can be detected and measured. A suitable period of time for contacting the agent with the cell can be determined empirically, and is generally a time sufficient to allow entry of the agent into the cell and to allow the agent to have a measurable effect on mitochondrial NAD-dependent deacetylase mRNA and/or polypeptide levels. Generally, a suitable time is between 10 minutes and 24 hours, or from about 1 hour to about 8 hours.

Methods of measuring mitochondrial NAD-dependent deacetylase mRNA levels are known in the art, several of which have been described above, and any of these methods can be used in the methods of the present invention to identify an agent which modulates mitochondrial NAD-dependent deacetylase mRNA level in a cell, including, but not limited to, a PCR, such as a PCR employing detectably labeled oligonucleotide primers, and any of a variety of hybridization assays.

Similarly, mitochondrial NAD-dependent deacetylase polypeptide levels can be measured using any standard method, several of which have been described herein, including, but not limited to, an immunoassay such as enzyme-linked immunosorbent assay (ELISA), for example an ELISA employing a detectably labeled antibody specific for a mitochondrial NAD-dependent deacetylase polypeptide.

Mitochondrial NAD-dependent deacetylase polypeptide levels can also be measured in cells harboring a recombinant construct comprising a nucleotide sequence that encodes a mitochondrial NAD-dependent deacetylase fusion protein, where the fusion partner provides for a detectable signal or can otherwise be detected. For example, where the fusion partner provides an immunologically recognizable epitope (an "epitope tag"), an antibody specific for an epitope of the fusion partner can be used to detect and quantitate the level of mitochondrial NAD-dependent deacetylase. In some embodiments, the fusion partner provides for a detectable signal, and in these embodiments, the detection method is chosen based on the type of signal generated by the fusion partner. For example, where the fusion partner is a fluorescent protein, fluorescence is measured.

Fluorescent proteins suitable for use include, but are not limited to, a green fluorescent protein (GFP), including, but not limited to, a "humanized" version of a GFP, e.g., wherein codons of the naturally-occurring nucleotide sequence are changed to more closely match human codon bias; a GFP derived from *Aequoria victoria* or a derivative thereof, e.g., a "humanized" derivative such as Enhanced GFP, which are available commercially, e.g., from Clontech, Inc.; a GFP from another species such as *Renilla reniformis, Renilla mullei*, or *Ptilosarcus guernyi*, as described in, e.g., WO 99/49019 and Peelle et al. (2001) *J Protein Chem.* 20:507-519; "humanized" recombinant GFP (hrGFP) (Stratagene); any of a variety of fluorescent and colored proteins from Anthozoan species, as described in, e.g., Matz et al. (1999) *Nature Biotechnol.* 17:969-973; and the like. Where the fusion partner is an enzyme that yields a detectable product, the product can be detected using an appropriate means, e.g., β-galactosidase can, depending on the substrate, yield colored product, which is detected spectrophotometrically, or a fluorescent product; luciferase can yield a luminescent product detectable with a luminometer; etc.

Agents that reduce a level of mitochondrial NAD-dependent deacetylase protein include agents that reduce a level of enzymatically active mitochondrial NAD-dependent deacetylase. In some embodiments, an agent that reduces a level of enzymatically active mitochondrial NAD-dependent deacetylase is an agent that inhibits activity of a mitochondrial processing peptidase (MPP). Whether MPP activity is inhibited can be determined using any known assay, e.g., detecting formation of the 28 kD active form of mitochondrial NAD-dependent deacetylase.

A number of methods are available for analyzing nucleic acids for the presence and/or level of a specific mRNA in a cell. The mRNA may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985), *Science* 239:487, and a review of techniques may be found in Sambrook, et al. *Molecular Cloning: A Laboratory Manual*, CSH Press 1989, pp. 14.2-14.33. Alternatively, various methods are known in the art that utilize oligonucleotide ligation as a means of detecting polymorphisms, for examples see Riley et al. (1990), *Nucl. Acids Res.* 18:2887-2890; and Delahunty et al. (1996), *Am. J. Hum. Genet.* 58:1239-1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2', 4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^3$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

A variety of different methods for determining the nucleic acid abundance in a sample are known to those of skill in the art, where particular methods of interest include those described in: Pietu et al., Genome Res. (June 1996) 6: 492-503; Zhao et al., Gene (Apr. 24, 1995) 156: 207-213; Soares, Curr. Opin. Biotechnol. (October 1997) 8: 542-546; Raval, J. Pharmacol Toxicol Methods (November 1994) 32: 125-127; Chalifour et al., Anal. Biochem (Feb. 1, 1994) 216: 299-304; Stolz & Tuan, Mol. Biotechnol. (December 19960 6: 225-230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

A number of methods are available for determining the expression level of a gene or protein in a particular sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. Alternatively, the secondary antibody conjugated to a fluorescent compound, e.g. fluorescein, rhodamine, Texas red, etc. The absence or presence of antibody binding may be determined by various methods, including flow cytometry of dissociated cells, microscopy, radiography, scintillation counting, etc.

Methods of Detecting Agents that Modulate an Activity of a Mitochondrial NAD-Dependent Deacetylase Polypeptide Methods of detecting an agent that modulates an activity of a mitochondrial NAD-dependent deacetylase polypeptide include cell-free and cell-based methods. The methods generally involve contacting a mitochondrial NAD-dependent deacetylase polypeptide with a test agent and determining the effect, if any, on the mitochondrial NAD-dependent deacetylase enzyme activity.

The deacetylase activity of a mitochondrial NAD-dependent deacetylase can be determined by incubating the enzyme in the presence of NAD and an acetylated substrate. Suitable acetylated substrates include acetylated histone 4, or a fragment thereof, e.g., amino acids 1-22 of histone 4. The amino acid sequence of amino acids 1-22 of histone 4 is: NH$_2$-MSGRGKGGKGLGKGGAKRHRKV—COOH (SEQ ID NO:02). Additional exemplary suitable substrates include the following: NH$_2$-MSGRGKGGKGLGKG-GAKRHRKVLRDNIQGI—COOH (from histone-4; SEQ ID NO:03); and NH$_2$-MARTKQTARKSTG-GKAPRKQLATKAARKSA-COOH (from histone-3; SEQ ID NO:04). In the foregoing peptides, the acetylated lysine residues are in italics.

The acetylated histone peptide is present in the assay mixture at a concentration of from about 20 µM to about 1 mM, from about 30 µM to about 900 µM, from about 40 µM to about 700 µM, from about 50 µM to about 500 µM, from about 50 µM to about 300 µM, or from about 60 µM to about 100 µM. NAD is present in the assay mixture at a concentration of about 1 mM. The acetyl group on the histone peptide is radiolabeled, e.g., [$^{14}$C]-acetyl is used. The assay then involves determining the amount of [$^{14}$C]-acetyl that is released, typically by scintillation counting. Other components, such as salts, reducing agents, and buffers, may be included.

In one exemplary embodiment, the enzymatic reaction mixture comprises 4 mM MgCl$_2$, 0.2 mM DTT, 50 mM Tris-HCl, pH 9.0, amino acids 1-22 of histone 4, which peptide is acylated with a radiolabel acetyl group, and 1 mM NAD.

Another method of detecting mitochondrial NAD-dependent deacetylase activity is to monitor the acetylation status of a histone substrate using an antibody specific for acetylated histone substrate. Lack of reactivity of the anti-acetylated histone antibody with the histone substrate indicates that the histone has been deacetylated. Thus, in some embodiments, the methods involve determining binding of an anti-acetylated histone antibody with the histone substrate. Anti-acetylated antibody/histone binding can be determined using any type of immunological assay, including immunoblotting assays, ELISA assays, and the like.

In some embodiments, the assay is a cell-free assay, wherein the mitochondrial NAD-dependent deacetylase is contacted with the test agent, the substrate (i.e., acetylated histone 4 peptide), and other reaction components (e.g., NAD, buffers, and the like), and the activity of the mitochondrial NAD-dependent deacetylase determined. In these embodiments, the mitochondrial NAD-dependent deacetylase may be purified, but need not be. The mitochondrial NAD-dependent deacetylase may be present in a cell extract; in an immunoprecipitate of a cell extract; or may be partially purified, e.g., at least about 50%, at least about 60%, at least about 70%, at least about 80%, at least about 90%, or more, purified, e.g., free of other macromolecules present in the source of the mitochondrial NAD-dependent deacetylase. The mitochondrial NAD-dependent deacetylase may be recombinant, or may be isolated from a natural source, e.g., a mammalian cell or tissue that normally produced the enzyme.

Agents

The present invention further provides biologically active agents identified using a method of the instant invention. A biologically active agent of the invention modulates a level or an activity of a mitochondrial NAD-dependent deacetylase. Agents are useful to treat various disorders, including cancer, neurodegenerative disorders, metabolic disorders, and disorders associated with apoptosis.

In many embodiments, the agent is a small molecule, e.g., a small organic or inorganic compound having a molecular weight of more than 50 and less than about 2,500 daltons. Agents may comprise functional groups necessary for structural interaction with proteins, particularly hydrogen bonding, and may include at least an amine, carbonyl, hydroxyl or carboxyl group, and may contain at least two of the functional chemical groups. The agents may comprise cyclical carbon or heterocyclic structures and/or aromatic or polyaromatic structures substituted with one or more of the above functional groups. Agents are also found among biomolecules including peptides, saccharides, fatty acids, steroids, purines, pyrimidines, derivatives, structural analogs or combinations thereof.

In some embodiments, an active agent is a peptide. Suitable peptides include peptides of from about 3 amino acids to about 50, from about 5 to about 30, or from about 10 to about 25 amino acids in length. A peptide of interest inhibits an enzymatic activity of mitochondrial NAD-dependent deacetylase.

Peptides can include naturally-occurring and non-naturally occurring amino acids. Peptides may comprise D-amino acids, a combination of D- and L-amino acids, and various "designer" amino acids (e.g., β-methyl amino acids, Cα-methyl amino acids, and Nα-methyl amino acids, etc.) to convey special properties to peptides. Additionally, peptide may be a cyclic peptide. Peptides may include non-classical amino acids in order to introduce particular conformational motifs. Any known non-classical amino acid can be used. Non-classical amino acids include, but are not limited to, 1,2,3,4-tetrahydroisoquinoline-3-carboxylate; (2S,3S)-methylphenylalanine, (2S,3R)-methyl-phenylalanine, (2R,3S)-methyl-phenylalanine and (2R,3R)-methyl-phenylalanine; 2-aminotetrahydronaphthalene-2-carboxylic acid; hydroxy-1,2,3,4-tetrahydroisoquinoline-3-carboxylate; β-carboline (D and L); HIC (histidine isoquinoline carboxylic acid); and HIC (histidine cyclic urea). Amino acid analogs and peptidomimetics may be incorporated into a peptide to induce or favor specific secondary structures, including, but not limited to, LL-Acp (LL-3-amino-2-propenidone-6-carboxylic acid), a β-turn inducing dipeptide analog; β-sheet inducing analogs; β-turn inducing analogs; α-helix inducing analogs; γ-turn inducing analogs; Gly-Ala turn analog; amide bond isostere; tretrazol; and the like.

A peptide may be a depsipeptide, which may be a linear or a cyclic depsipeptide. Kuisle et al. (1999) *Tet. Letters* 40:1203-1206. "Depsipeptides" are compounds containing a sequence of at least two alpha-amino acids and at least one alpha-hydroxy carboxylic acid, which are bound through at least one normal peptide link and ester links, derived from the hydroxy carboxylic acids, where "linear depsipeptides" may comprise rings formed through S—S bridges, or through an hydroxy or a mercapto group of an hydroxy-, or mercapto-amino acid and the carboxyl group of another amino- or hydroxy-acid but do not comprise rings formed only through peptide or ester links derived from hydroxy carboxylic acids. "Cyclic depsipeptides" are peptides containing at least one ring formed only through peptide or ester links, derived from hydroxy carboxylic acids.

Peptides may be cyclic or bicyclic. For example, the C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride ($CH_2Cl_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Methods for making cyclic peptides are well known in the art The term "bicyclic" refers to a peptide in which there exists two ring closures. The ring closures are formed by covalent linkages between amino acids in the peptide. A covalent linkage between two nonadjacent amino acids constitutes a ring closure, as does a second covalent linkage between a pair of adjacent amino acids which are already linked by a covalent peptide linkage. The covalent linkages forming the ring closures may be amide linkages, i.e., the linkage formed between a free amino on one amino acid and a free carboxyl of a second amino acid, or linkages formed between the side chains or "R" groups of amino acids in the peptides. Thus, bicyclic peptides may be "true" bicyclic peptides, i.e., peptides cyclized by the formation of a peptide bond between the N-terminus and the C-terminus of the peptide, or they may be "depsi-bicyclic" peptides, i.e., peptides in which the terminal amino acids are covalently linked through their side chain moieties.

A desamino or descarboxy residue can be incorporated at the terminii of the peptide, so that there is no terminal amino or carboxyl group, to decrease susceptibility to proteases or to restrict the conformation of the peptide. C-terminal functional groups include amide, amide lower alkyl, amide di(lower alkyl), lower alkoxy, hydroxy, and carboxy, and the lower ester derivatives thereof, and the pharmaceutically acceptable salts thereof.

In addition to the foregoing N-terminal and C-terminal modifications, a peptide or peptidomimetic can be modified with or covalently coupled to one or more of a variety of hydrophilic polymers to increase solubility and circulation half-life of the peptide. Suitable nonproteinaceous hydrophilic polymers for coupling to a peptide include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. Generally, such hydrophilic polymers have an average molecular weight ranging from about 500 to about 100,000 daltons, from about 2,000 to about 40,000 daltons, or from about 5,000 to about 20,000 daltons. The peptide can be derivatized with or coupled to such polymers using any of the methods set forth in Zallipsky, S., Bioconjugate Chem., 6:150-165 (1995); Monfardini, C, et al., Bioconjugate Chem., 6:62-69 (1995); U.S. Pat. Nos. 4,640,835; 4,496,689; 4,301,144; 4,670,417; 4,791,192; 4,179,337 or WO 95/34326.

Another suitable agent for reducing an activity of a mitochondrial NAD-dependent deacetylase is a peptide aptamer. Peptide aptamers are peptides or small polypeptides that act as dominant inhibitors of protein function. Peptide aptamers specifically bind to target proteins, blocking their function ability. Kolonin and Finley, PNAS (1998) 95:14266-14271. Due to the highly selective nature of peptide aptamers, they may be used not only to target a specific protein, but also to target specific functions of a given protein (e.g. a signaling function). Further, peptide aptamers may be expressed in a controlled fashion by use of promoters which regulate expression in a temporal, spatial or inducible manner. Peptide aptamers act dominantly; therefore, they can be used to analyze proteins for which loss-of-function mutants are not available.

Peptide aptamers that bind with high affinity and specificity to a target protein may be isolated by a variety of techniques known in the art. Peptide aptamers can be isolated from random peptide libraries by yeast two-hybrid screens (Xu et al., PNAS (1997) 94:12473-12478). They can also be isolated from phage libraries (Hoogenboom et al., Immunotechnology (1998) 4:1-20) or chemically generated peptides/libraries.

Intracellularly expressed antibodies, or intrabodies, are single-chain antibody molecules designed to specifically bind and inactivate target molecules inside cells. Intrabodies have been used in cell assays and in whole organisms. Chen et al., Hum. Gen. Ther. (1994) 5:595-601; Hassanzadeh et al., Febs Lett. (1998) 16(1, 2):75-80 and 81-86. Inducible expression vectors can be constructed with intrabodies that react specifically with mitochondrial NAD-dependent deacetylase protein. These vectors can be introduced into model organisms and studied in the same manner as described above for aptamers.

In some of the invention, the active agent is an agent that modulates, and generally decreases or down regulates, the expression of the gene encoding mitochondrial NAD-dependent deacetylase in the host. Such agents include, but are not limited to, antisense RNA, interfering RNA, ribozymes, and the like.

In some embodiments, the active agent is an interfering RNA (RNAi). RNAi includes double-stranded RNA interference (dsRNAi). Use of RNAi to reduce a level of a particular mRNA and/or protein is based on the interfering properties of double-stranded RNA derived from the coding regions of gene. In one example of this method, complementary sense and antisense RNAs derived from a substantial portion of the mitochondrial NAD-dependent deacetylase gene are synthesized in vitro. The resulting sense and antisense RNAs are annealed in an injection buffer, and the double-stranded RNA injected or otherwise introduced into the subject (such as in their food or by soaking in the buffer containing the RNA). See, e.g., WO99/32619. In another embodiment, dsRNA derived from a mitochondrial NAD-dependent deacetylase gene is generated in vivo by simultaneous expression of both sense and antisense RNA from appropriately positioned promoters operably linked to mitochondrial NAD-dependent deacetylase coding sequences in both sense and antisense orientations.

Antisense molecules can be used to down-regulate expression of the gene encoding mitochondrial NAD-dependent deacetylase in cells. Antisense compounds include ribozymes, external guide sequence (EGS) oligonucleotides (oligozymes), and other short catalytic RNAs or catalytic oligonucleotides which hybridize to the target nucleic acid and modulate its expression.

The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which modifications alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The β-anomer of deoxyribose may be used, where the base is inverted with respect to the natural α-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Exemplary modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Oligonucleotides having a morpholino backbone structure (Summerton, J. E. and Weller D. D., U.S. Pat. No. 5,034, 506) or a peptide nucleic acid (PNA) backbone (P. E. Nielson, M. Egholm, R. H. Berg, O. Buchardt, Science 1991, 254: 1497) can also be used. Morpholino antisense oligonucleotides are amply described in the literature. See, e.g., Partridge et al. (1996) *Antisense Nucl. Acid Drug Dev.* 6:169-175; and Summerton (1999) *Biochem. Biophys. Acta* 1489:141-158.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43-56.

Formulations, Dosages, and Routes of Administration

The invention provides formulations, including pharmaceutical formulations, comprising an agent that reduces a level and/or an activity of mitochondrial NAD-dependent deacetylase. In general, a formulation comprises an effective amount of an agent that reduces a level and/or an activity of mitochondrial NAD-dependent deacetylase. An "effective amount" means a dosage sufficient to produce a desired result, e.g., a reduction in a level and/or an activity of mitochondrial NAD-dependent deacetylase, a reduction in histone deacetylation; and the like. Generally, the desired result is at least a reduction a level and/or an activity of mitochondrial NAD-dependent deacetylase as compared to a control.

Formulations

In the subject methods, the active agent(s) may be administered to the host using any convenient means capable of resulting in the desired reduction in a level and/or an activity of mitochondrial NAD-dependent deacetylase. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Other modes of administration will also find use with the subject invention. For instance, an agent of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

An agent of the invention can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range is one which provides up to about 1 µg to about 1,000 µg or about 10,000 µg of an agent that reduces a level and/or an activity of mitochondrial NAD-dependent deacetylase can be administered in a single dose. Alternatively, a target dosage of an agent that reduces a level and/or an activity of mitochondrial NAD-dependent deacetylase can be considered to be about in the range of about 0.1-1000 µM, about 0.5-500 µM, about 1-100 µM, or about 5-50 µM in a sample of host blood drawn within the first 24-48 hours after administration of the agent.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Routes of Administration

An agent that reduces a level and/or an activity of mitochondrial NAD-dependent deacetylase is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intratumoral, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as an allergic hypersensitivity. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, e.g. in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Therapeutic Methods

The invention further provides methods of treating various disorders, by modulating a level or an activity of a mitochondrial NAD-dependent deacetylase. The methods generally involve administering to an individual in need thereof an effective amount of an agent that modulates a level or an activity of a mitochondrial NAD-dependent deacetylase. In some embodiments, the methods involve decreasing a level or activity of a mitochondrial NAD-dependent deacetylase. In other embodiments, the methods involve increasing a level or activity of a mitochondrial NAD-dependent deacetylase.

Increasing a level or activity of a mitochondrial NAD-dependent deacetylase provides a protective effect against apoptosis. In some embodiments, an effective amount of an agent that increases a level of activity of a mitochondrial NAD-dependent deactylase is an amount that is effective to decrease apoptosis by at least about 10%, at least about 20%, at least about 30%, at least about 40%, at least about 50%, at least about 60%, at least about 70%, at least about 80%, or at least about 90% or more, when compared to the level of apoptosis in an individual not treated with the agent.

Decreasing a level or activity of a mitochondrial NAD-dependent deacetylase increases apoptosis. Increasing apoptosis is desirable in the context of reducing unwanted cellular proliferation. In some embodiments, an effective amount of an agent that decreases a level of activity of a mitochondrial NAD-dependent deactylase is an amount that is effective to increase apoptosis by at least about 10%, at least about 20%, at least about 30%, at least about 40%, at least about 50%, at least about 60%, at least about 70%, at least about 80%, or at least about 90% or more, when compared to the level of apoptosis in an individual not treated with the agent.

Disorders amenable to treatment using a method according to the invention are disorders related to, associated with, or caused (directly or indirectly) by mitochondrial malfunction or dysfunction. Disorders amenable to treatment using a method according to the invention include cancer; neurodegenerative disorders; metabolic disorders; ischemia-reperfusion injury; and disorders associated with apoptosis or cell death.

Indications which can be treated using the methods of the invention for reducing apoptosis or cell death in a eukaryotic cell, include, but are not limited to, cell death or apoptosis associated with Alzheimer's disease, Parkinson's disease, rheumatoid arthritis, septic shock, sepsis, stroke, central nervous system inflammation, osteoporosis, ischemia (e.g., resulting from stroke or myocardial infarction), reperfusion injury, cell death associated with cardiovascular disease, polycystic kidney disease, cell death of endothelial cells in cardiovascular disease, degenerative liver disease, multiple sclerosis, amyotropic lateral sclerosis, cerebellar degeneration, ischemic injury, cerebral infarction, myocardial infarction, myelodysplastic syndromes, aplastic anemia, male pattern baldness, and head injury damage. Also included are any hypoxic or anoxic conditions, e.g., conditions relating to or resulting from ischemia, myocardial infarction, cerebral infarction, stroke, bypass heart surgery, organ transplantation, neuronal damage, and the like.

Cell death-related indications which can be treated using methods of the invention for activating apoptosis or cell death include, but are not limited to, undesired, excessive, or uncontrolled cellular proliferation, including, for example, neoplastic cells; as well as any undesired cell or cell type in which induction of cell death is desired, e.g., virus-infected cells and self-reactive immune cells. The methods may be used to treat follicular lymphomas, carcinomas associated with p53 mutations; autoimmune disorders, such as, for example, systemic lupus erythematosus (SLE), immunemediated glomerulonephritis; hormone-dependent tumors, such as, for example, breast cancer, prostate cancer and ovary cancer; and viral infections, such as, for example, herpesviruses, poxviruses and adenoviruses.

Whether a therapeutic method of the invention is effective in modulating cell death/apoptosis can be determined using any known assay. Cell death can be measured using any known method, and is generally measured using any of a variety of known methods for measuring cell viability. Such assays are generally based on entry into the cell of a detectable compound (or a compound that becomes detectable upon interacting with, or being acted on by, an intracellular component) that would normally be excluded from a normal, living cell by its intact cell membrane. Such compounds include substrates for intracellular enzymes, including, but not limited to, a fluorescent substrate for esterase; dyes that are excluded from living cell, including, but not limited to, trypan blue; and DNA-binding compounds, including, but not limited to, an ethidium compound such as ethidium bromide and ethidium homodimer, and propidium iodide.

Apoptosis can be assayed using any known method. Assays can be conducted on cell populations or an individual cell, and include morphological assays and biochemical assays. A non-limiting example of a method of determining the level of apoptosis in a cell population is TUNEL (TdT-mediated dUTP nick-end labeling) labeling of the 3'-OH free end of DNA fragments produced during apoptosis (Gavrieli et al. (1992) *J. Cell Biol.* 119:493). The TUNEL method consists of catalytically adding a nucleotide, which has been conjugated to a chromogen system or a to a fluorescent tag, to the 3'-OH end of the 180-bp (base pair) oligomer DNA fragments in order to detect the fragments. The presence of a DNA ladder of 180-bp oligomers is indicative of apoptosis. Procedures to detect cell death based on the TUNEL method are available commercially, e.g., from Boehringer Mannheim (Cell Death Kit) and Oncor (Apoptag Plus). Another marker that is currently available is annexin, sold under the trademark APOPTEST™. This marker is used in the "Apoptosis Detection Kit," which is also commercially available, e.g., from R&D Systems. During apoptosis, a cell membrane's phospholipid asymmetry changes such that the phospholipids are exposed on the outer membrane. Annexins are a homologous group of proteins that bind phospholipids in the presence of calcium. A second reagent, propidium iodide (PI), is a DNA binding fluorochrome. When a cell population is exposed to both reagents, apoptotic cells stain positive for annexin and negative for PI, necrotic cells stain positive for both, live cells stain negative for both. Other methods of testing for apoptosis are known in the art and can be used, including, e.g., the method disclosed in U.S. Pat. No. 6,048,703.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric. Standard abbreviations may be used, e.g., bp, base pair(s); kb, kilobase(s); pl, picoliter(s); s, second(s); min, minute(s); hr, hour(s); and the like.

Example 1

Characterization of a Mitochondrial NAD-Dependent Histone Deacetylase

Experimental Procedures

Plasmid Construction

Plasmids expressing hSIRT3 were constructed by polymerase chain reaction (PCR) amplification of the hSIRT3 coding sequence using primers containing EcoRI sites and pCR2.1-SIRT3 as a template. Amplified sequences were digested with EcoRI and cloned into a modified pcDNA3.1+ vector (Invitrogen, Carlsbad, Calif.) to yield a C-terminally FLAG-tagged hSIRT3. hSIRT3Δ1-25-FLAG was constructed by using modified N-terminal PCR primers introducing EcorI sites and a methionine start codon before amino acid 26 of the wild-type protein. Site-directed mutagenesis (QuikChange™ Mutagenesis Kit, Stratagene, La Jolla, Calif.) was used for construction of hSIRT3N229A-FLAG, hSIRT3H248Y-FLAG, hSIRT3R7/13G-FLAG, hSIRT3R17/21 G-FLAG, hSIRT3R7/13/17/21 G-FLAG, hSIRT3R7/13Q-FLAG, hSIRT3R17/21 Q-FLAG, hSIRT3R7/13/17/21-FLAG, hSIRT3L12P/R13P-FLAG and hSIRT3R99/100G-FLAG. All constructs were verified by DNA sequencing. pSu9-DHFR was provided by J. Brix and N. Pfanner (Institut fuer Biochemie und Molekularbiologie, Freiburg, Germany).

GFP Fusion Constructs

To generate fusion proteins of GFP with wild-type hSIRT3 or with amino acid 26-399 of hSIRT3, corresponding coding sequences were PCR amplified and cloned into pEGFP—N1 (Clontech, Palo Alto, Calif.).

Cell Culture and Transfection

HEK293T and HeLa cells were cultured in DMEM supplemented with 10% FCS, 2 mM L-glutamine, 100 U Penicillin and 100 μg Streptomycin per ml and grown in 5% $CO_2$ at 37° C. Calcium phosphate transfection was used to transfect HEK293T cells (19). HeLa cells were transfected with Lipofectamine (Life Technologies, Rockville, Md.).

Immunoblot Analysis

Antibodies used for immunoblotting included anti-mtHsp70 (Clone JG1, Affinity Bioreagents, Golden, Colo.), anti-Hsp60 (Clone 4B9/89, Affinity Bioreagents, Golden, Colo.), anti-Hsp90α (StressGen, Victoria, Canada), anti-cytochrome c oxidase subunit IV (Clone 20E8-C12, Molecular Probes, Eugene, Oreg.), anti-FLAG M2 (Sigma, St. Louis, Mo.), anti-cytochrome c (Clone 7H8.2C12, Pharmingen, San Diego, Calif.). hSIRT3 antisera were raised in rabbits against a C-terminal peptide ($H_2N$-DLVQRETGKLDGPDK—COOH; SEQ ID NO:05). Western blots were revealed with enhanced chemiluminescence (Amersham Pharmacia, Piscataway, N.J.). Membranes were either nitrocellulose (Hybond ECL, Amersham Pharmacia, Piscataway, N.J.) or PVDF (Immun-Blot™, Bio-Rad, Hercules, Calif.).

Immunofluorescence and Confocal Microscopy

HeLa cells grown on coverslips were incubated for 45 min with 30 nM MitoTracker (CMXRos, Molecular Probes, Inc., Eugene, Oreg.) in DMEM min at 37° C., transferred to fresh DMEM and further incubated for 60 min. Cells on coverslips were rinsed in phosphate-buffered saline (PBS), fixed in 3.7% formaldehyde/PBS for 30 min, washed again in PBS and mounted. Images were acquired on a BioRad Radiance 2000 laser scanning microscope equipped with an Olympus BX60 microscope using an Olympus PlanApo 60×/1.40 oil objective. Excitation laser line was 488 nm for enhanced green fluorescent protein (eGFP) and 578 nm for MitoTracker.

Preparation of Subcellular Fractions

Subcellular fractionation was performed according to published procedures with minor modifications (20,21). All steps were performed at 4° C. In brief, cells were homogenized in ice-cold buffer A (250 mM sucrose, 10 mM KCl, 1.5 mM $MgCl_2$, 1 mM EDTA, 1 mM EGTA, 1 mM dithiotreithol, 0.1 mM phenylmethylsulfonyl fluoride, 20 mM HEPES-KOH, pH 7.5) and homogenized in a Dounce homogenizer (Wheaton, Millville, N.J.). Homogenization was checked by phase-contrast microscopy. The homogenate was centrifuged twice at 800×g to remove nuclei and unbroken cells. Mitochondria were sedimented by centrifugation at 7,000×g for 15 min at 4° C., washed twice with buffer A and resuspended in TXIP-1 buffer (1% Triton X-100 (v/v), 150 mM NaCl, 0.5 mM EDTA, 50 mM Tris-HCl, pH 7.4) supplemented with protease inhibitors. Postmitochondrial supernatants were fractionated by ultracentrifugation at 100,000×g for 30 min at 4° C. The supernatant constituting the cytosolic S-100 fraction was removed and the pellet was resuspended in TXIP-1 buffer. Protein concentrations of the fractions were determined (DC Protein Assay, Bio-Rad, Hercules, Calif.) and equal amounts of each fraction were separated by SDS-PAGE and blotted to nitrocellulose.

Isolation of Mitochondria from Mammalian Cells

Mitochondria were isolated by differential centrifugation according to published procedures (21). After several washes in SEM buffer (250 mM sucrose, 1 mM EDTA, 10 mM MOPS-KOH, pH 7.2), mitochondria were resuspended in SEM buffer. To further purify mitochondria, a crude mitochondrial fraction was layered on a discontinuous sucrose gradient (1-1.5 M) in $T_{10}E_1$ buffer (1 mM EDTA, 10 mM Tris-HCl, pH 7.5). After centrifugation for 20 min at 60,000×g at 4° C., mitochoridria were recovered from the 1.0 M/1.5 M interface, carefully adjusted to 250 mM sucrose and washed twice in SEM buffer.

Immunoprecipitation

Cells or isolated mitochondria were lysed in ice-cold TXIP-1 buffer containing either PMSF or protease inhibitor cocktail (Roche, Indianapolis, Ind.). Lysates were centrifuged at 16,000×g for 5 min at 4° C. and Anti-FLAG monoclonal M2 antibody (Sigma, St. Louis, Mo.) covalently coupled to agarose was added. Samples were incubated at 4° C. for 12 hrs, centrifuged and washed 4 times in TXIP-1 buffer. For the deacetylation assays, the fourth wash was carried out in SIRT deacetylase buffer (4 mM MgC12, 0.2 mM dithiothreitol, 50 mM Tris-HCl, pH 9.0)

Import of Radiolabeled Proteins into Isolated Mitochondria

Import into isolated mitochondria was carried out as previously reported (22). Proteins were synthesized in the presence of [$^{35}$S]-methionine by coupled transcription-translation in reticulocyte lysate (Promega, Madison, Wis.) (23). In vitro translation reactions were centrifuged at 108,000×g, 2° C. for 15 min and adjusted to 250 mM sucrose. Import reactions contained 5% (v/v) reticulocyte lysate in import buffer (3% (w/v) fatty-acid free bovine serum albumin (BSA), 250 mM sucrose, 80 mM KCl, 5 mM $MgCl_2$, 2 mM $KH_2PO_4$, 5 mM L-methionine, 10 mM 3-[N-morpholino] propanesulfonic acid-KOH, pH 7.2). In each import reaction, 50 µg of freshly isolated mammalian mitochondria were mixed with radiolabeled proteins and incubated at 30° C. ATP (2 mM) and sodium succinate (10 mM) were added to maintain coupling of isolated mitochondria. Import was stopped by addition of valinomycin (1 µM) and transfer to 0°C.

Where indicated, samples were treated with proteinase K (50 µg/ml) for 10 min on ice. Protease treatment was stopped by addition of 2 mM phenylmethylsulfonyl fluoride (PMSF). Mitochondria were reisolated by centrifugation at 10,000×g for 5 min at 4° C., washed in SEM buffer and recentrifuged as above. Mitochondrial pellets were resuspended in SDS sample buffer containing dithiothreitol (DTT) and heated to 95° C. for 5 min. Samples were subjected to SDS-PAGE. Dried gels were exposed to Biomax MR film (Kodak, Rochester, N.Y.) at −70° C. and analyzed on a Fuji FUJIX BAS 1000 phosphorimager. Where indicated, mitochondrial transmembrane potential was disrupted by blocking of complex III of the respiratory chain (Antimycin, 8 µM), blocking of the $F_0/F_1$-ATPase (Oligomycin, 20 µM) and potassium flux (Valinomycin, 1 µM).

Swelling experiments were performed according to published protocols (24). Mitochondria were isolated from hSIRT3-FLAG transfected HEK293T cells, washed and treated with proteinase K (150 µg/ml) to remove nonimported protein. Mitochondria were reisolated at 10 000×g for 5 min, washed with SEM buffer and recentrifuged. Mitochondrial pellets were resuspended in SM buffer (250 mM sucrose, 10 mM MOPS-KOH, pH 7.2) and swollen by diluting them tenfold dilution into M buffer (10 mM MOPS-KOH, pH 7.2) and incubation on ice for 15 min. Mitoplasts and non swollen mitochondria were treated with proteinase K (150 µg/ml) for 10 min at 0° C. Protease digestion was stopped by addition of 2 mM PMSF and mitoplasts and mitochondria were reisolated by centrifugation, washed and lysed in sample buffer. Samples were separated by SDS-PAGE and blotted onto PVDF membrane. Radiolabeled proteins were detected by autoradiography.

Fractionation of Mitochondrial Proteins by Alkaline Treatment

These experiments were performed using published protocols (25,26). In brief, washed mitochondrial pellets were resuspended in freshly prepared 0.1 M sodium carbonate, pH 11.5, and incubated at 0° C. for 30 min. Mitochondrial membranes were sedimented by ultracentrifugation at 100,000×g for 30 min at 4° C. The pellet was resuspended in SDS sample buffer and proteins in the supernatant were concentrated by trichloracetate precipitation and finally resuspended in sample buffer.

In Vitro Deacetylase Assay

Deacetylase assays were performed in a total volume of 100 µl SIRT deacetylase buffer (4 mM $MgCl_2$, 0.2 mM dithiothreitol, 50 mM Tris-HCl, pH 9.0) containing immunoprecipitated proteins or mitochondrial lysates and a peptide corresponding to the first the first 22 amino acids of histone 4 chemically acetylated in vitro (27). Where indicated, 1 mM NAD, 5 mM nicotinamide (both from Sigma, St. Louis, Mo.) or 400 nM TSA (WAKO, Richmond, Va.) were added. Deacetylation reactions were stopped after 2 hours of incubation at room temperature by adding 25 µl stop solution (0.1 M HCl, 0.16 M acetic acid). Released acetate was extracted into 500 µl ethyl acetate and samples were vigorously shaken for 15 minutes. After centrifugation for 5 minutes, 400 µl of the ethyl acetate fraction was mixed with 5 ml scintillation fluid (Packard, Meriden, Conn.) and the released radioactivity was measured using a liquid scintillation counter.

Mitochondrial Processing Peptidase Cleavage Assay

Purified recombinant yeast MPP (28) was obtained from G. Isaya (Mayo Clinic and Foundation, Rochester, Minn.). Cleavage of radiolabeled in vitro translated proteins was carried out in reaction buffer (1 mM dithiothreitol, 1 mM $MnCl_2$, 10 mM Hepes-KOH, pH 7.4). Purified MPP or reaction buffer was added to each sample followed by incubation at 27° C. for 45 min. Reactions were stopped by addition of SDS sample buffer and boiling at 95° C. for 5 min. Samples were separated by SDS-PAGE and analyzed by phosphorimaging.

Results

Mitochondria Contain Sir2-like Deacetylase Activity.

A systematic survey of subcellular fractions for the presence of histone deacetylase activities led to the detection of a deacetylase activity in human mitochondrial fractions prepared from HEK293 T cells (FIG. 1A). This activity was strictly dependent on the presence of NAD and was suppressed by nicotinamide (Vitamin B3), a product of NAD hydrolysis (29-31) reported to inhibit Sir2-like proteins (32) (FIG. 1A). In contrast, trichostatin A (TSA), a specific inhibitor of class I and class II deacetylases, had no effect on the deacetylase activity present in mitochondria (FIG. 1A). Under the same conditions, TSA treatment led to a significant inhibition of the activity of a prototypic class II HDAC, HDAC6. The observed NAD-dependent deacetylase activity sensitive to inhibition by nicotinamide but not by TSA indicated the presence of Sir2-like class III protein deacetylases in mitochondria.

hSIRT3 Mediates NAD-Dependent Deacetylase Activity in the Mitochondria.

Transfection of each hSIRT cDNA in mammalian cells followed by immunoprecipitation and incubation with a histone H4 peptide substrate showed that hSIRT 1, 2 and 3 exhibited bona fide NAD-dependent deacetylase activity while hSIRT4, 5, 6 and 7 showed no detectable activity. To determine which hSIRT protein contributed to the mitochondrial activity, expression vectors for hSIRT 1, hSIRT2 and hSIRT3 (epitope-tagged with FLAG at the C-terminus), or a control vector, were transfected into HEK293T cells. Cells were harvested and half of the preparation was used to prepare a whole cell lysate while the other half was used to isolate and purify mitochondria (mitochondrial lysate). hSIRT proteins were immunoprecipitated with anti-FLAG antibodies from whole cell or from mitochondria lysates and tested by western blotting for the presence of the protein. All three proteins were expressed and detected in whole cell lysates (FIG. 1B). Interestingly, two forms of hSIRT3 were detected, a 44 KDa product of the expected size given the cDNA sequence (predicted molecular weight=43.6 KDa) and a smaller, 28 KDa product (FIG. 11B).). In contrast, anti-FLAG immunoprecipitates prepared from mitochondria, showed only the presence of hSIRT3 (28 KDa product) but not of hSIRT1 and 2 (FIG. 1B). Testing of the same immunoprecipitates for enzymatic activity yielded the same results. While all three hSIRTs showed robust NAD-dependent enzymatic activity after immunoprecipitation from whole cell lysates (FIG. 1C), only anti-FLAG immunoprecipitates from cells transfected with hSIRT3 showed mitochondrial deacetylase activity (FIG. 1D). These results are consistent with the model that hSIRT3 can target mitochondria and mediate NAD-dependent deacetylase activity within that subcellular compartment.

When total mitochondrial lysates prepared from cells transfected with hSIRT3 were analyzed in the same in vitro deacetylase assay, an increase in NAD-dependent deacetylase activity was observed in comparison to cells transfected with a control plasmid (FIG. 1E). The mitochondrial lysates overexpressing hSIRT3 exhibited the same properties as untransfected mitochondrial lysates in terms of sensitivity to nicotinamide and TSA. In contrast, transfection of two catalytically inactive mutants, hSIRT3-N229A and hSIRT3-H248Y, had no effect on the activity of the lysates (FIG. 1E). These two mutants were designed by homology to similar mutations reported to abrogate the activity of Sir2-like proteins. Both mutants were shown in separate experiments to be catalytically inactive in whole cell lysates. Importantly, both mutants were efficient targeted to mitochondria, were equally well expressed after transfection and were processed to the smaller 28 KDa product as wild type hSIRT3 (FIG. 1F). These observations are consistent with the selective targeting of exogenous hSIRT3 to mitochondria.

FIG. 1A: Mitochondria contain Sir2-like deacetylase activity. Mitochondrial lysates were prepared from HEK293T cells and protein content was determined. Equal amounts of lysate were assayed for deacetylase activity on a histone H4 peptide in either the presence or absence of NAD (1 mM) or in combination with nicotinamide (5 mM) or TSA (400 mM). Samples were incubated for 2 hrs at 25° C. Released acetate was quantitated as described in Materials and Methods. Representative results are shown.

FIG. 1B: In vitro deacetylase activity assay. hSIRT proteins were immunoprecipitated from whole cell lysate from transfected HEK293T cells using anti-FLAG antibodies. Immunoprecipitated proteins were assayed in the presence or absence of NAD (1 mM).

FIG. 1C: Purified mitochondria from HEK293T cells transfected with hSIRT proteins were lysed and FLAG-tagged proteins were immunoprecipitated and analyzed for in vitro deacetylase activity.

FIG. 1D: Western blot analysis of the immunoprecipitates obtained from whole cell lysate (upper panel) or purified mitochondria (lower panel). 50% of the immunoprecipitate used in the deacetylase assay was detected using anti-FLAG M2 antibodies.

FIG. 1E: Transfection of hSIRT3 increases the NAD-dependent deacetylase activity of mitochondria. Mitochondria were isolated from HEK293T cells transfected with hSIRT3-FLAG, hSIRT3N229A-FLAG, hSIRT3H248Y-FLAG or control vector (pFLAG) and lysed in TXIP-1 buffer. In vitro deacetylase activities of equal amounts of mitochondrial lysate are shown.

FIG. 1F: Mitochondria were analyzed for the presence of hSIRT3 wild-type and mutants by western blotting.

Endogenous and Exogenous hSIRT3 are Mitochondrial Proteins.

To further determine the subcellular localization of hSIRT3 in cells, a fusion protein with green fluorescent protein was generated (hSIRT3-GFP). Confocal laser scanning microscopy of HeLa cells transfected with hSIRT3-GFP revealed that it localized exclusively to cytoplasmic substructures consistent with mitochondria. This prediction was verified by costaining with a mitochondria-specific dye, MitoTracker red, which showed total overlapping of the two signals. This experiment indicated that hSIRT3 exclusively localizes to mitochondria.

This observation was further verified using cell fractionation experiments. Cells transfected with hSIRT3-FLAG were used to prepare subcellular fractions according to established protocols (21). Equal amounts of protein from each subcellular fraction were subjected to SDS-PAGE and immunoblotting using an antibody specific for the C-terminal FLAG-epitope. hSIRT3-FLAG and cytochrome c were only be detected within the heavy membrane fraction representing mitochondria (HM, FIG. 2A). Two FLAG-reactive bands were detected within the mitochondrial fraction as discussed above (see FIG. 2A). Immunoblotting of subfractions prepared from untransfected cell confirmed that both bands were specific for hSIRT3-FLAG.

Endogenous Mitochondrial hSIRT3 Protein has NAD-Dependent Deacetylase Activity.

Figure 2B:
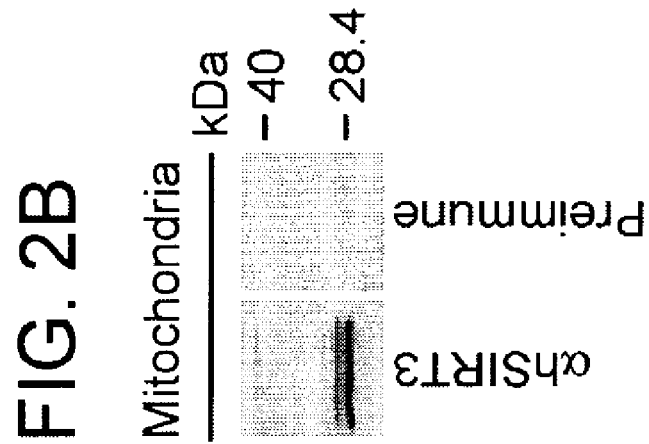

To examine the subcellular localization of endogenous hSIRT3, a specific antiserum was raised against the a peptide corresponding the last 15 amino acids of hSIRT3 (N-DLVQRETGKLDGPDK-C; SEQ ID NO:06). This antiserum recognized two peptides of 44 and 28 KDa in mitochondria fraction while the preimmune antiserum obtained from the same rabbit was unreactive to these proteins (FIG. 2B). These two bands corresponded in size to the ~44 and 28 kDa fragment detected after transfection of the FLAG-tagged hSIRT3. Immunoprecipitation of mitochondria fraction with this antiserum showed the presence of a specific NAD-dependent deacetylase activity which was not present with the preimmune serum or with Protein G sepharose alone (FIG. 2C). These experiments demonstrate that endogenous hSIRT3 is located in the mitochondria and is associated with NAD-dependent deacetylase activity in that compartment.

Figure 2A:
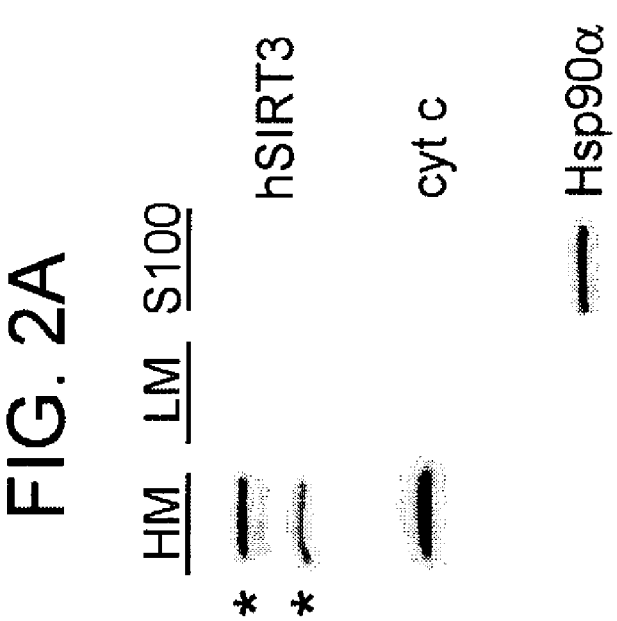

FIG. 2A: Subcellular fractionation of HEK293T cells transfected with hSIRT3-FLAG were homogenized and fractionated by differential centrifugation. Equal amounts (30 μg) of HM (heavy membranes), LM (light membranes) and S-100 (cytosolic proteins) fraction were analyzed by immunoblotting. hSIRT3-FLAG was revealed by detection with monoclonal M2 anti-FLAG antibodies. Two hSIRT3-FLAG specific forms (asterisks) were detected. Nitrocellulose membranes were stripped and reprobed with antibodies against cytochrome c (cyt c) and Hsp90α.

FIG. 2B: Detection of endogenous hSIRT3 protein in mitochondrial lysates. Mitochondria were prepared from HEK293T cells. Lysates were were analyzed by western blotting using a polyclonal rabbit hSIRT3 antiserum (35 μg/ml) or a preimmune serum (35 μg/ml) obtained from the same rabbit.

FIG. 2C: Endogenous hSIRT3 protein has NAD-dependent deacetylase activity in vitro. hSIRT3 was immunoprecipitated from HEK293T cells lysed in TXIP-1 buffer using hSIRT3 antiserum (0.35 mg/ml), preimmune serum (0.35 mg/ml) or protein G sepharose. Equal amounts of immunoprecipitate were analyzed for in vitro deacetylase activity.

The N-Terminus of hSIRT3 is Required for Mitochondrial Import.

Figure 3:
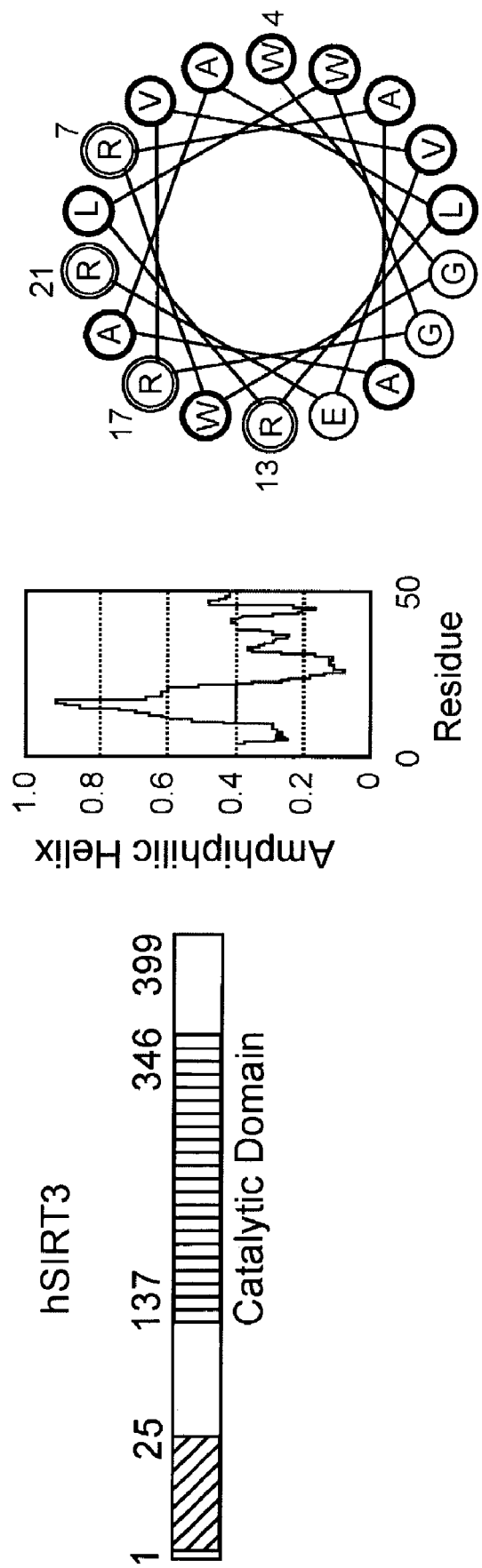
FIG. 3 depicts requirement of the N-terminal region of hSIRT3 for mitochondrial targeting.

Mitochondrial targeting signals frequently contain an amphipatic α-helix and tend to contain positively charged, hydrophobic and hydroxylated amino acid residues (15-18). Secondary structure prediction of hSIRT3 revealed that an N-terminal peptide corresponding to residues 1-25 has a high probability to contain an amphipatic alpha-helix (34, 35) (FIG. 3, middle panel). When plotted as a helical wheel (FIG. 3, right panel) residues 4 to 21, showed a cluster of positively charged arginine residues on one side of the helix opposed by hydrophobic residues on the other side, a typical feature of mitochondrial presequences (reviewed in (36)). To test the importance of this putative alpha-helix in hSIRT3 mitochondrial import, amino acid residues 1- to 25 were deleted from hSIRT3 and fused it to GFP (hSIRT3Δ1-25-GFP). Expression of this construct in HeLa cells showed pancellular distribution. No significant colocalization between the fusion protein and MitoTracker-stained mitochondria could be observed. This localization was in sharp contrast to the subcellular localization observed after expression of full-length hSIRT3 protein fused to GFP and indicated that the N-terminal 25 amino acids of hSIRT3 are necessary for mitochondrial targeting.

FIG. 3. The N-terminal region of hSIRT3 is required for mitochondrial targeting. Schematic diagram of hSIRT3. The hatched box illustrates the region involved in mitochondrial targeting (left panel). Parts of the N-terminal region show a high probability to form an amphiphatic α helix (middle panel). Illustration of residues 4 to 21 as a helical wheel plot reveals a cluster of basic amino acids (black) on one side of the putative helix (right panel).

Figure 4A:
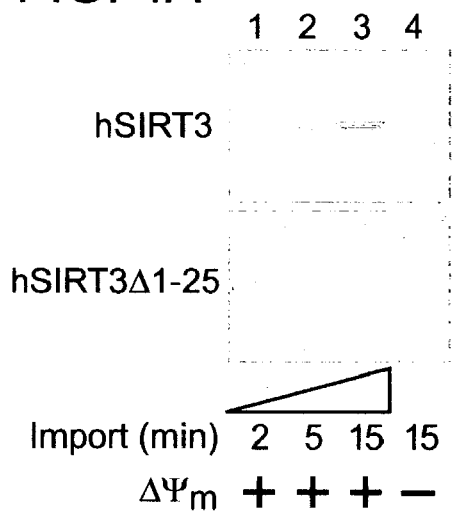
FIGS. 4A-C depict mitochondrial import of hSIRT3.

To further define the requirement for mitochondrial import of hSIRT3, cell-free mitochondrial in vitro import assays were used. Similar assays have been used to elucidate the import requirements of a variety of mitochondrial proteins. [$^{35}$S]-labeled hSIRT3 or hSIRT3Δ1-25 proteins were synthesized in rabbit reticulocyte lysates and incubated with isolated mammalian mitochondria at 30° C. for 2, 5 or 15 minutes in the presence of succinate and ATP. Mitochondria were reisolated from the mixture by centrifugation and cosedimenting proteins were analyzed by sodium dodecyl sulfatepolyacrylamide gel electrophoresis (SDS-PAGE) analysis followed by autoradiography. A time-dependent accumulation of hSIRT3, but not of hSIRT3 μl-25, into mitochondria was observed (FIGS. 4A and B). The import of SIRT across the mitochondrial membrane was dependent on the mitochondrial transmembrane potential (ΔΨm) since import was inhibited in the presence of antimycin (8 μM), oligomycin, (20 μM) and valinomycin (1 μM). (FIG. 4A, lane 4).

When the proteinase K digestion performed at the end of the import reaction was omitted, it was noted that both hSIRT3 and hSIRT3Δ1-25 could bind to the outer surface of mitochondria in vitro, indicating that adhesion to mitochondria was not dependent on the N-terminal 25 amino acids of hSIRT3. To exclude the possibility that proteins had aggregated and cosedimented nonspecifically, similar experiments were carried out in the absence of mitochondria, but no unspecific sedimentation occurred.

To further define the sequence and structural requirements necessary for import of hSIRT3 into mitochondria, a series of point mutations in the first 25 amino acids was generated. We used two different strategies. First, we disrupted the α helix by introducing 2 prolines at position 12 and 13. Second, we modified the charge of the amphipathic helix by replacing arginine residues with glycine or glutamine. The polar but uncharged glutamine residues were predicted to preserve the α helical conformation while changing the amphipathic character of the α helix. To study the import efficiency, mutants and wild type hSIRT3 were synthesized in rabbit reticulocyte lysates in the presence of [$^{35}$S]-methionine and assayed using the in vitro import assay described above. Mutation of R7 and R13 in either glycine or glutamine resulted in a loss of mitochondrial import. In contrast, mutation of R17 and R21 reduced import by ~50% (FIG. 4C). When all arginine residues were mutated into glutamine or glycine import efficiency was even further reduced. Disruption of the putative helical structure by two prolines led to a loss in mitochondrial import similar to the R7/13G mutant. These results demonstrate the importance of the positively charged residues and of the α helical structure of region 1-25 in hSIRT3 for its import into mitochondria.

Figure 4B:
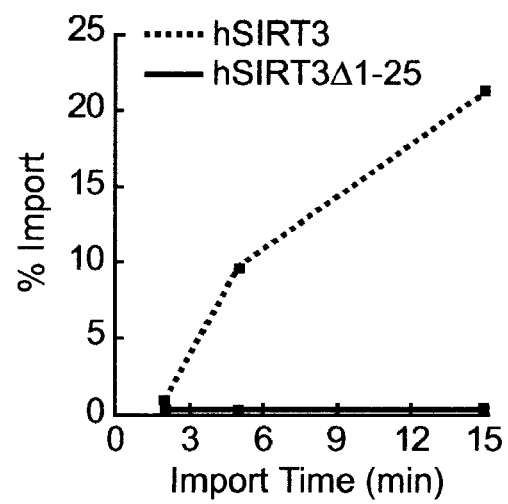
Figure 4C:
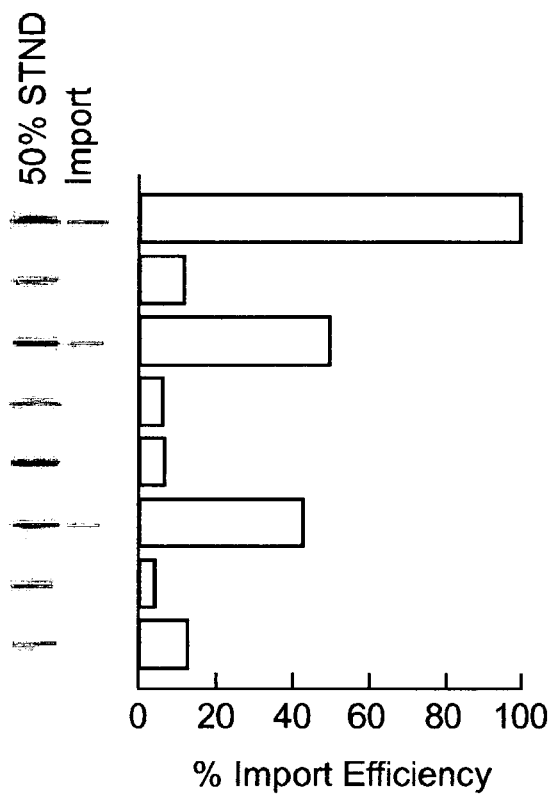

FIG. 4. Mitochondrial import of hSIRT3. FIG. 4A, [$^{35}$S]-labeled hSIRT3-FLAG or hSIRT3Δ1-25-FLAG synthesized in rabbit reticulocyte lysate was imported into isolated mammalian mitochondria at 30° C. To assay import in the absence of Δψm (lane 4), valinomycin (1 μM), antimycin (8 μM) and oligomycin (20 μM) were added to mitochondria 5 min prior to the addition of proteins. At indicated timepoints, further import was stopped by dissipating Δψm (addition of 1 μM valinomycin) and incubation at 0° C. Samples from each timepoint were treated with proteinase K (50 μg/ml) for 10 min at 0° C. to remove nonimported proteins. After reisolation of mitochondria and SDS-PAGE, the amounts of imported proteins were quantified by phosphorimaging. FIG. 4B, Quantitation of imported protein by phosphorimaging. FIG. 4C, Schematic illustration of mutants used to address the effects of charged residues and conformation on hSIRT3 import. FIG. 4D, [$^{35}$S]-labeled hSIRT3 wild-type or mutants were imported into isolated mitochondria for 20 min at 30° C. Import was stopped as described above and nonimported proteins were removed by proteinase K treatment. Reisolated and washed mitochondria were lysed in SDS sample buffer and analyzed by SDS-PAGE. Standards representing 50% of the input used in the individual import reactions were loaded adjacent to each import sample. FIG. 4E, Import efficiency of individual hSIRT3 mutants was quantitated in relation to their standards by phosphorimaging. The import efficiency of hSIRT3 was set to 100%.

hSIRT3 is a Mitochondrial Matrix Protein

Figure 5A:
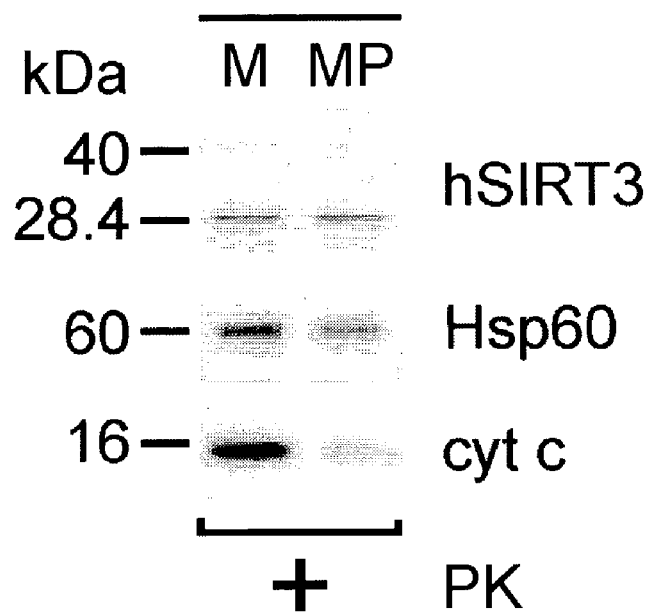
FIGS. 5A and 5B depict intramitochondrial localization of hSIRT3.

As discussed above, the observation that the mitochondrial transmembrane potential (ΔΨm) was required for hSIRT3 import into mitochondria suggested that hSIRT3 is likely to be imported across the inner mitochondrial membrane. To further define the exact localization of hSIRT3 in the mitochondria, we took advantage of established methods addressing the submitochondrial localization of proteins. First, mitochondria were isolated from HEK293T cells expressing hSIRT3-FLAG. Mitoplasts were prepared by incubation in hypotonic MOPS-buffer. This treatment leads to the rupture of the outer mitochondrial membrane and to the release of soluble proteins located in the intermembrane space. Mitoplasts and mitochondria were reisolated by centrifugation and analyzed by western blotting (FIG. 5A). The ~28 kDa form of hSIRT3 was not affected by the breakage of the outer mitochondrial membrane and subsequent proteinase K digestion (FIG. 5A).

To exclude the possibility that hSIRT3-FLAG had formed a protease-stable aggregate, mitochondria from cells transfected with hSIRT3-FLAG were lysed in 0.5% Triton X-100 followed by proteinase K digestion. Under these conditions, hSIRT3 was completely degraded. In this respect, hSIRT3 behaved in a manner similar to the matrix protein Hsp60 (FIG. 5A). Confirmation of the rupture of the outer membrane by the hypotonic treatment was obtained by blotting against the intermembrane space protein cytochrome c. In contrast to hSIRT3, cytochrome c was lost after protease treatment of mitoplasts (FIG. 5A). The results were consistent with three different locations for hSIRT3: 1. mitochondrial matrix; 2. peripherally attached to the inner side of the inner mitochondrial membrane; 3. integral inner mitochondrial membrane protein.

Figure 5B:
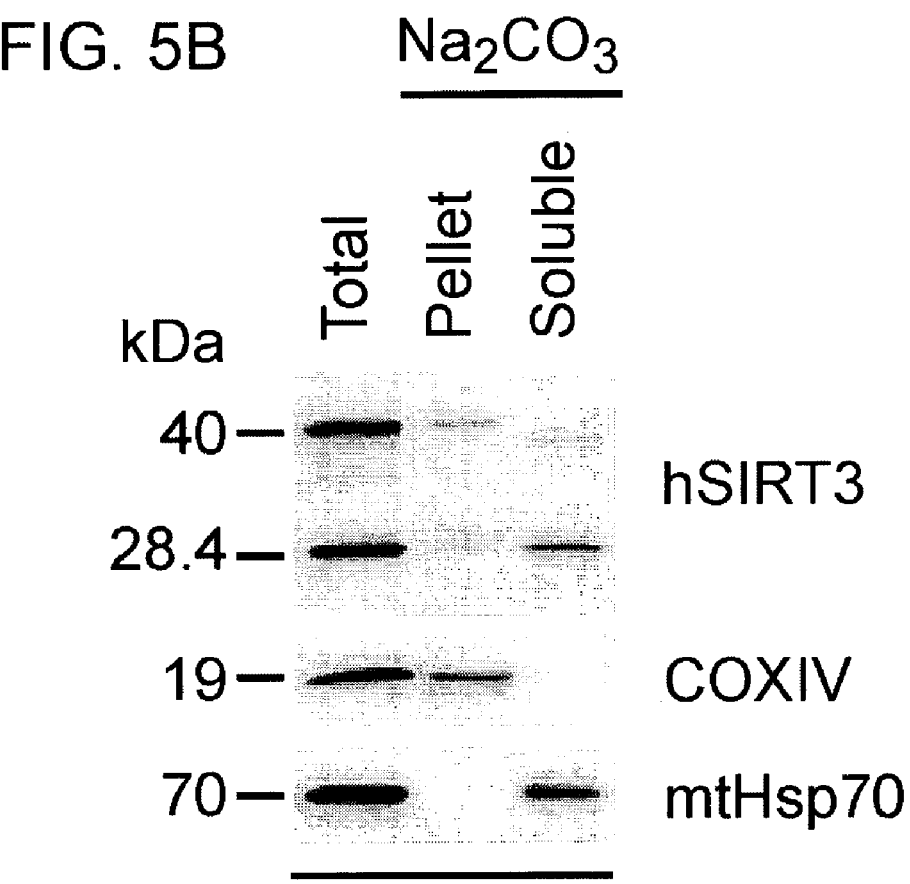

To differentiate between these possibilities, we performed alkaline extraction experiments of mitochondria with sodium carbonate at pH 11.5. This treatment releases soluble and peripheral membrane proteins to the supernatant, while integral membrane proteins sediment with the membranes in the pellet (25). Following this treatment, the ~28 KDa form of hSIRT3 was found in the supernatant, indicating that this form was either a soluble matrix protein or was peripherally attached to the inner face of the inner membrane (FIG. 5A). Interestingly, the ~44 KDa form of hSIRT3 was detected mostly in the pellet, suggesting that this form of SIRT3 is associated with the inner mitochondrial membrane. As expected, the soluble matrix chaperonin mtHsp70 was detected in the supernatant after alkaline extraction, whereas the inner-membrane protein COXIV was associated with the membrane fraction (FIG. 5B). These experiments indicate that the 28 KDa form or hSIRT3 is a soluble matrix protein.

FIG. 5. A, Intramitochondrial localization of hSIRT3. Mitochondria were isolated from hSIRT3-FLAG transfected HEK293T cells and treated with proteinase K (150 μg/ml) for 10 min at 0° C. to remove proteins bound to the outer mitochondrial surface. Proteinase K treatment was stopped by incubation with 2 mM PMSF for 10 min at 0° C. Mitochondrial preparations were divided and one half was diluted with hypotonic EM buffer to create mitoplasts. The other half was mock-treated with isotonic SEM buffer. After incubation for 20 min at 0° C., proteinase K (150 μg/ml) was added for 10 min at 0° C. Protease treatment was stopped as described above and mitochondria (M, left lane) and mitoplasts (MP, right lane) were reisolated and analyzed by western blotting. Opening of the outer mitochondrial membrane was confirmed by detection of endogenous intermembrane space protein cytochrome c (cyt c). Integrity of the inner mitochondrial membrane was determined using the matrix protein Hsp60 as a marker. hSIRT3-FLAG was detected using anti-FLAG M2 antibodies.

FIG. 5B, Alkaline extraction of mitochondria from hSIRT3-FLAG transfected HEK293T cells. Mitochondria were isolated and treated with proteinase K (150 μg/ml) for 10 min at 0° C. PMSF (2 mM) was added to stop proteinase K digestion. Mitochondria were reisolated and washed in SEM buffer. The preparation was devided and one half was resuspended in SDS sample buffer (Total, left lane). The other half of the preparation was resuspended in 100 mM sodium carbonate ($Na_2CO_3$), pH 11.5, and incubated for 30 min at 0° C. The extract was centrifuged at 100,000×g at 4° C. and the mitochondrial membranes (Pellet, middle lane) were resuspended in SDS sample buffer. The supernatant containing the soluble and peripheral membrane proteins was TCA precipitated (Soluble, right lane). Samples were analyzed by western blotting. hSIRT3 was detected using anti-FLAG antibodies. Alkaline extraction was controlled by detection of the marker proteins COXIV and mtHsp70.

Proteolytic Processing of hSIRT3

Figure 6A:
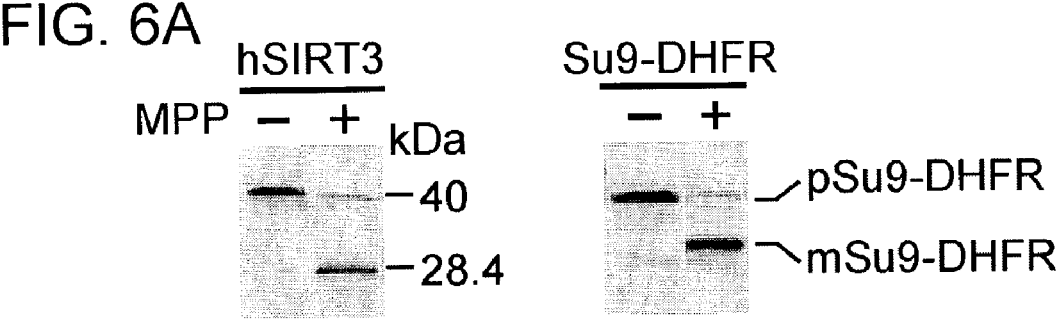
FIGS. 6A-C depict proteolytic processing of hSIRT3 by MPP.

As discussed above, the majority of hSIRT3 is present in mitochondria as a truncated ~28 KDa protein. Since this form is reactive to the anti-FLAG antibody after transfection of a C-terminal FLAG fusion protein, we concluded that hSIRT3 is proteolytically cleaved at its N-terminus. The majority of mitochondrial proteins carrying N-terminal targeting signals is processed by matrix processing peptidase (MPP) after import into the mitochondrial matrix (38). Incubation of radiolabelled hSIRT3 with recombinant yeast MPP led to its cleavage to a product of ~28 KDa, undistinguishable in size from the product detect in vivo in mitochondria (FIG. 6A). Cleavage of a fusion protein between subunit 9 of F0/F1-ATPase and DHFR (Su9-DHFR) by MPP in vitro resulted in the appearance of digestion products similar to what has been previously reported (28). Based on the size of the processed hSIRT3 protein, we scanned the primary sequence of hSIRT3 for putative MPP recognition motifs. MPP specifically processes many mitochondrial precursor proteins but no consensus processing site has emerged. However, an arginine at −2 relative to the cleavage site and additional aromatic or hydrophobic residues in position 1 relative to the cleavage site appear necessary for cleavage (39-41).

Several hSIRT3 mutants targeting arginine residues at positions 99, 100, 133, 135, 139 and 158 were constructed by site-directed mutagenesis and synthesized in rabbit reticulocyte in the the presence of [$^{35}$S]-methionine. A mutant carrying two glycines substituted for arginines at position 99 and 100 showed abrogation of cleavage by MPP in vitro (FIG. 6B), while other mutants were unaffected. These results indicate that residues R99/100 are critical for the processing of hSIRT3 by MPP. Transfection of this construct into mammalian cells led to a partial inhibition of the processing of hSIRT3 into the 28 KDa fragment and a new fragment of higher molecular weight was detected.

Catalytic Activation of a Latent hSIRT3 by MPP-Mediated Proteolytic Processing

It was noted that the in vitro translated hSIRT3 protein was catalytically inactive in our in vitro deacetylase assay. Similarly, hSIRT3 expressed in *E. coli* was not processed and was poorly active enzymatically. The hypothesis that proteolytic processing of hSIRT3 might lead to its catalytic activation was tested. Unlabeled hSIRT3 was synthesized in vitro using rabbit reticulocyte lysate. Samples were split in half and subjected to cleavage by recombinant MPP in vitro. Reactions were diluted and hSIRT3 was immunoprecipitated and assayed for deacetylase activity in the presence or absence of NAD. Remarkably, the hSIRT3 processed by MPP showed NAD-dependent deacetylase activity, whereas the full-length uncleaved hSIRT3 remained inactive (FIG. 6C). These results linked processing of hSIRT3 to the activation of its NAD-dependent deacetylase activity. To control that no unspecific factors or MPP itself had caused the observed NAD-dependent deacetylase activity, we used the catalytic inactive hSIRT3H248Y mutant. When this mutant was assayed in the same way as hSIRT3, no NAD-dependent deacetylase activity after incubation and cleavage with MPP (FIG. 6C, left and right panels). These results demonstrate that proteolytic processing of hSIRT3 by MPP leads to the activation of its latent enzymatic activity.

Figure 6B:
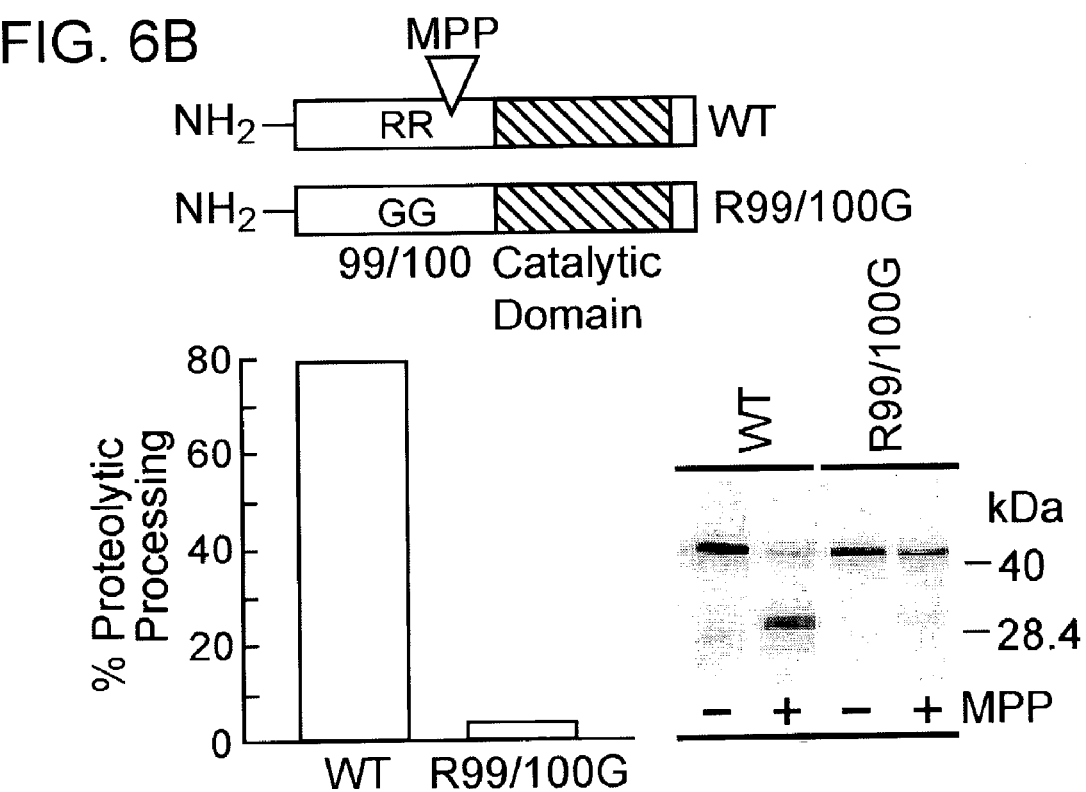
Figure 6C:
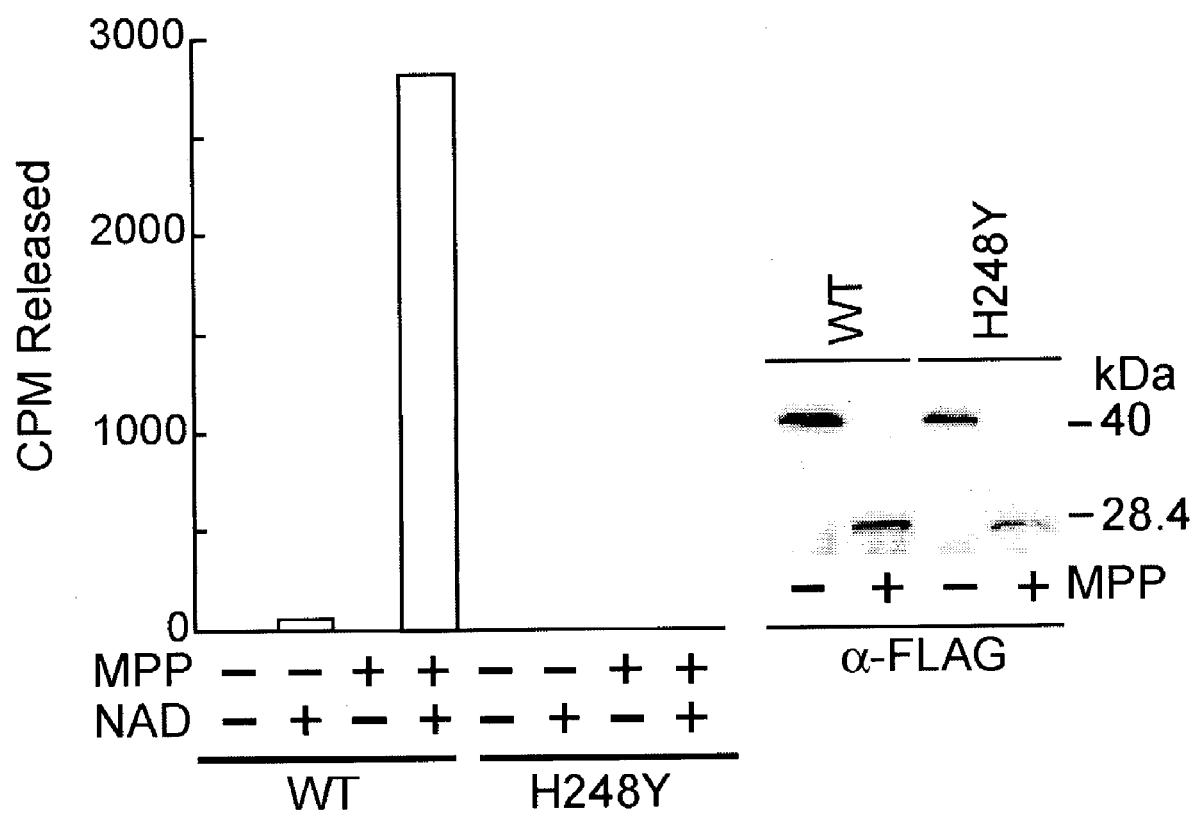

FIG. 6. Proteolytic processing of hSIRT3 by MPP. FIG. 6A, Cleavage of radiolabeled hSIRT3-FLAG (left panel) or pSu9-DHFR (right panel) was assayed in HDM buffer in the presence or absence of purified recombinant yeast MPP (1 µl) for 45 min at 27° C. in a total volume of 20 µl. Samples were analyzed by SDS-PAGE and autoradiography. p, precursor form; m, mature form of pSu9-DHFR. FIG. 6B, Schematic illustration of the mutant showing abrogated MPP cleavage (upper panel). Radiolabeled wild-type hSIRT3-FLAG or hSIRT3R99/100G-FLAG were analyzed for MPP processing. Assay conditions were as described (see A). Efficiency of proteolytic processing by recombinant yeast MPP was quantitated using phosphorimaging (left panel). Autoradiography of the same experiment (right panel). FIG. 6C, MPP processing activates NAD-dependent deacetylase activity of hSIRT3. Unlabeled hSIRT3-FLAG or hSIRT3H248Y-FLAG synthesized in rabbit reticulocyte lysate was incubated with recombinant yeast MPP or an equal amount of water for 45 min at 27° C. Samples were diluted with TXIP-1 buffer. FLAG-tagged proteins were immunoprecipitated with anti-FLAG M2 antibodies covalently bound to agarose for 2 hrs at 4° C. Immunoprecipitates were washed and analyzed for in vitro deacetylase activity in the presence or absence of NAD (1 mM). FIG. 6D, Western blot analysis of immunoprecipitates used in the deacetylase assay.

Example 2

Enzymatically Active Recombinant SIRT 3 Protein hSIRT3 is an NAD dependent, class III HDAC. SIRT3 localizes to the mitochondrial matrix via an amphipathic α-helix rich NH$_2$-terminal. Once in the mitochondrial matrix, hSIRT3 is proteolytically cleaved by mitochondrial matrix processing peptidase (MPP) between residues Ser101 and Ile102. Full length hSIRT3 is enzymatically inactive, but exhibits HDAC activity in vitro after MPP cleavage. Based on these observations, it was predicted that a recombinant form of SIRT3 lacking the first 100 amino acids to mimic the cleavage that occurs in the mitochondria would be active as an HDAC.

Cloning Strategy

PCR primers were designed to amplify hSIRT3 from Ser101 to Lys399 using a pcDNA3.1-SIRT3-Flag plasmid (pEV821) as a template. Primer sequence is as follows: forward—GTGAATTCATATCTTTTTCTGTGGGTGC (SEQ ID NO:07), reverse—GTGAATTCGCCCTTGAAT-CATC (SEQ ID NO:08). Both primers included an EcoR1 site so the PCR amplicon could be digested with EcoR1 for subclonig into other vectors. The following PCR parameters were used: 94° C.-5', (94° C.-30", 55° C.-30", 72° C. -60")×30 cycles, 72° C.-7'. The EcoR1 digested amplicon was then subcloned into the expression vector pTrcHis. Frame form B of pTrcHis was used for subcloning to express an in frame, amino terminal 6×His tagged SIRT3 (101-399 aa) recombinant protein.

Expression and Purification

DH5α bacteria were transformed with the pTrcHis-SIRT3 (101-399) plasmid (pEV1453). Transformed bacteria were induced with 1.0 mM IPTG at 37 C for 2 h. The resulting 6×His-tagged protein was purified under native conditions at 4° C. by Ni—NTA affinity chromatography (Qiagen).

First, bacteria were pelleted and cleared lysate was prepared under native conditions. The pellet was resuspended (50 mM NaH$_2$PO$_4$, pH8.0; 300 mM NaCl; 10 mM imidazole) and incubated on ice for 30 minutes in the presence of 1 mg/ml lysozyme. This mixture was then sonicated on ice (four 10-15 second bursts at40-60% power) and centrifuged at 4° C. at 14,000 rpm for 25 minutes. Supernatant (cleared lysate) was bound to Ni—NTA resin (batch method, Qiagen) on a rotary mixer at 4° C. for 60 minutes. Batch mixture was loaded into poly prep column (BioRad) and flow-through collected. The resin bed was washed twice with 4 ml of wash buffer (50 mM NaH$_2$PO$_4$, pH8.0; 300 mM NaCl; 20 mM imidazole), and the tagged proteins eluted 4 times with 0.5 ml elution buffer (50 mM NaH$_2$PO$_4$, pH8.0; 300 mM NaCl; 250 mM imidazole). SDS-PAGE analysis revealed the second elution fraction contained a majority of recombinant protein along with contaminating proteins. A concentrating spin column (Vivaspin 6) was used to concentrate the recombinant protein and remove excess imidazole.

Activity Assay

Recombinant SIRT3 (1.5 µg) was resuspended in 100 µL deacetylase buffer (50 mM Tris-HCl [pH 9.0], 4 mM MgCl$_2$, and 0.2 mM DTT) with different concentrations of NAD (Sigma) and 20,000 cpm of the acetylated peptide substrate (in vitro acetylated histone H4 peptide).

Figure 8:
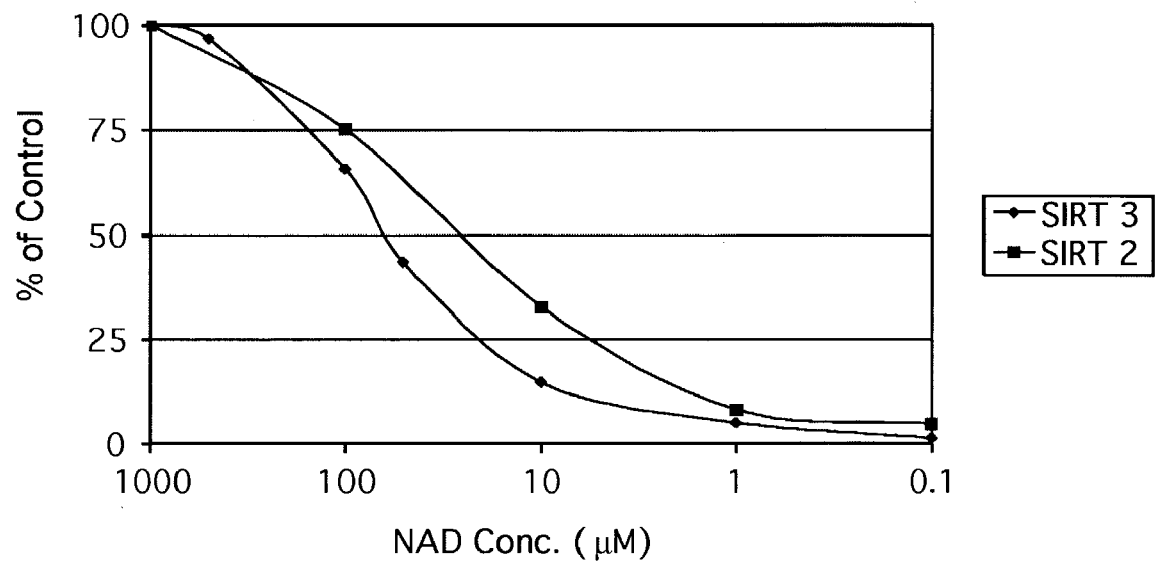
FIG. 8 depicts NAD-dependent HDAC activity of truncated recombinant SIRT3.

The results are shown in FIG. 8. SIRT3 showed a dose-dependent HDAC activity similar to the activity demonstrated for SIRT2. This experiment demonstrate that recombinant SIRT3 can function as a deacetylase in vitro and offers a new tool for the screening of SIRT3 inhibitors and the study of its enzymatic activity.

REFERENCES

1. Gottschling, D. E., Aparicio, O. M., Billington, B. L., and Zakian, V. A. (1990) *Cell* 63(4), 751-62.
2. Martin, S. G., Laroche, T., Suka, N., Grunstein, M., and Gasser, S. M. (1999) *Cell* 97(5), 621-33.
3. Lin, S. J., Defossez, P. A., and Guarente, L. (2000) *Science* 289(5487), 2126-8.
4. Kaeberlein, M., McVey, M., and Guarente, L. (1999) *Genes Dev* 13(19), 2570-80.
5. Tissenbaum, H. A., and Guarente, L. (2001) *Nature* 410(6825), 227-30.
6. Guarente, L. (2000) *Genes Dev* 14(9), 1021-6.
7. Imai, S., Armstrong, C. M., Kaeberlein, M., and Guarente, L. (2000) *Nature* 403(6771), 795-800.
8. Smith, J. S., Brachmann, C. B., Celic, I., Kenna, M. A., Muhammad, S., Starai, V. J., Avalos, J. L., Escalante-Semerena, J. C., Grubmeyer, C., Wolberger, C., and Boeke, J. D. (2000) *Proc Natl Acad Sci USA* 97(12), 6658-63.
9. Finnin, M. S., Donigian, J. R., Cohen, A., Richon, V. M., Rifkind, R. A., Marks, P. A., Breslow, R., and Pavletich, N. P. (1999) *Nature* 401(6749), 188-93.
10. Frye, R. A. (1999) *Biochem Biophys Res Commun* 260(1), 273-9.
11. Frye, R. A. (2000) *Biochem Biophys Res Commun* 273(2), 793-8.
12. North, B. J., and Verdin, E., unpublished observations.
13. Luo, J., Nikolaev, A. Y., Imai, S., Chen, D., Su, F., Shiloh, A., Guarente, L., and Gu, W. (2001) *Cell* 107(2), 137-48.
14. Vaziri, H., Dessain, S. K., Ng Eaton, E., Imai, S. I., Frye, R. A., Pandita, T. K., Guarente, L., and Weinberg, R. A. (2001) *Cell* 107(2), 149-59.
15. von Heijne, G., Steppuhn, J., and Herrmann, R. G. (1989) *Eur J Biochem* 180(3), 535-45.
16. Abe, Y., Shodai, T., Muto, T., Mihara, K., Torii, H., Nishikawa, S., Endo, T., and Kohda, D. (2000) *Cell* 100(5), 551-60.
17. Roise, D., Horvath, S. J., Tomich, J. M., Richards, J. H., and Schatz, G. (1986) *Embo J* 5(6), 1327-34.
18. Roise, D., Theiler, F., Horvath, S. J., Tomich, J. M., Richards, J. H., Allison, D. S., and Schatz, G. (1988) *Embo J* 7(3), 649-53.
19. Chen, C., and Okayama, H. (1987) *Mol Cell Biol* 7(8), 2745-52.
20. Condorelli, F., Salomoni, P., Cotteret, S., Cesi, V., Srinivasula, S. M., Alnemri E. S., and Calabretta, B. (2001) *Mol Cell Biol* 21(9), 3025-36.
21. Yang, J., Liu, X., Bhalla, K., Kim, C. N., Ibrado, A. M., Cai, J., Peng, T. I., Jones, D. P., and Wang, X. (1997) *Science* 275(5303), 1129-32.
22. Wiedemann, N., Pfanner, N., and Ryan, M. T. (2001) *Embo J* 20(5), 951-60.
23. Pelham, H. R., and Jackson, R. J. (1976) *Eur J Biochem* 67(1), 247-56.
24. Ryan, M. T., Voos, W., and Pfanner, N. (2001) in *Mitochondria, Methods In Cell Biology* (Pon, L. A., and Schon, E. A., eds) Vol. 65, pp. 189-216, Academic Press
25. Fujiki, Y., Hubbard, A. L., Fowler, S., and Lazarow, P. B. (1982) *J Cell Biol* 93(1), 97-102.
26. Honlinger, A., Bomer, U., Alconada, A., Eckerskom, C., Lottspeich, F., Dietmeier, K., and Pfanner, N. (1996) *Embo J* 15(9), 2125-37
27. Emiliani, S., Fischle, W., Van Lint, C., Al-Abed, Y., and Verdin, E. (1998) *Proc Natl Acad Sci USA* 95(6), 2795-800.
28. Geli, V. (1993) *Proc Natl Acad Sci USA* 90(13), 6247-51.
29. Tanny, J. C., and Moazed, D. (2001) *Proc Natl Acad Sci USA* 98(2), 415-20.
30. Tanner, K. G., Landry, J., Sternglanz, R., and Denu, J. M. (2000) *Proc Natl Acad Sci USA* 97(26), 14178-82.
31. Landry, J., Slama, J. T., and Sternglanz, R. (2000) *Biochem Biophys Res Commun* 278(3), 685-90.
32. Landry, J., Sutton, A., Tafrov, S. T., Heller, R. C., Stebbins, J., Pillus, L., and Sternglanz, R. (2000) *Proc Natl Acad Sci USA* 97(11), 5807-11.
33. Grozinger, C. M., Hassig, C. A., and Schreiber, S. L. (1999) *Proc Natl Acad Sci USA* 96(9), 4868-73.
34. Rost, B., and Sander, C. (1994) *Proteins* 19(1), 55-72.
35. Rost, B., and Sander, C. (1993) *J Mol Biol* 232(2), 584-99.
36. Pfanner, N., and Geissler, A. (2001) *Nat Rev Mol Cell Biol* 2(5), 339-49.
37. Martin, J., Mahlke, K., and Pfanner, N. (1991) *J Biol Chem* 266(27), 18051-7.
38. Jensen, R. E., and Johnson, A. E. (2001) *Nat Struct Biol* 8(12), 1008-10.
39. Hartl, F. U., Pfanner, N., Nicholson, D. W., and Neupert, W. (1989) *Biochim Biophys Acta* 988(1), 1-45.
40. Hendrick, J. P., Hodges, P. E., and Rosenberg, L. E. (1989) *Proc Natl Acad Sci USA* 86(11), 4056-60.
41. Gavel, Y., and von Heijne, G. (1990) *Protein Eng* 4(1), 33-7.
42. Arretz, M., Schneider, H., Wienhues, U., and Neupert, W. (1991) *Biomed Biochim Acta* 50(4-6), 403-12
43. Isaya, G., Kalousek, F., Fenton, W. A., and Rosenberg, L. E. (1991) *J Cell Biol* 113(1), 65-76.
44. Kalousek, F., Hendrick, J. P., and Rosenberg, L. E. (1988) *Proc Natl Acad Sci USA* 85(20), 7536-40.
45. Perrod, S., Cockell, M. M., Laroche, T., Renauld, H., Ducrest, A. L., Bonnard, C., and Gasser, S. M. (2001) *Embo J* 20(1-2), 197-209.
46. Afshar, G., and Murnane, J. P. (1999) *Gene* 234(1), 161-8.
47. Yang, Y. H., Chen, Y. H., Zhang, C. Y., Nimmakayalu, M. A., Ward, D. C., and Weissman, S. (2000) *Genomics* 69(3), 355-69.
48. Zemzoumi, K., Sereno, D., Francois, C., Guilvard, E., Lemesre, J. L., and Ouaissi, A. (1998) *Biol Cell* 90(3), 239-45.
49. Tischler, M. E., Friedrichs, D., Coll, K., and Williamson, J. R. (1977) *Arch Biochem Biophys* 184(1), 222-36.
50. Di Lisa, F., Menabo, R., Canton, M., Barile, M., and Bernardi, P. (2001) *J Biol Chem* 276(4), 2571-5.
51. Devin, A., Guerin, B., and Rigoulet, M. (1997) *FEBS Lett* 410(2-3), 329-32.
52. Vinogradov, A., Scarpa, A., and Chance, B. (1972) *Arch Biochem Biophys* 152(2), 646-54.
53. Bernardi, P. (1999) *Physiol Rev* 79(4), 1127-55.
54. Bernardi, P., Scorrano, L., Colonna, R., Petronilli, V., and Di Lisa, F. (1999) *Eur J Biochem* 264(3), 687-701.

55. Ziegler, M., Jorcke, D., and Schweiger, M. (1997) *Biochem J* 326(Pt 2), 401-5.
56. Lenaz, G. (1998) *Biochim Biophys Acta* 1366(1-2), 53-67
57. Wallace, D. C. (ed) (1997) *The Molecular and Genetic Basis of Neurological Disease*. eds. Rosenberg, R. N., Prusiner, S. B., DiMauro, S. & Barchi, R. L. Edited by eds. Rosenberg, R. N., Prusiner, S. B., DiMauro, S. & Barchi, R. L., Butterworth-Heinemann, Boston
58. Jackson, M. D., and Denu, J. M., personal communication.
59. Jackson, M. D., Denu, J. M., Schwer, B., and Verdin, E., unpublished observations.
60. Weksberg, R., Teshima, I., Williams, B. R., Greenberg, C. R., Pueschel, S. M., Chernos, J. E., Fowlow, S. B., Hoyme, E., Anderson, I. J., Whiteman, D. A., and et al. (1993) *Hum Mol Genet* 2(5), 549-56.
61. Henry, I., Bonaiti-Pellie, C., Chehensse, V., Beldjord, C., Schwartz, C., Utermann, G., and Junien, C. (1991) *Nature* 351(6328), 665-7.
62. Feinberg, A. P. (2000) *Curr Top Microbiol Immunol* 249, 87-99
63. Ferguson-Smith, A. C., Cattanach, B. M., Barton, S. C., Beechey, C. V., and Surani, M. A. (1991) *Nature* 351 (6328), 667-70.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process, step or steps, to the objective, spirit and scope of the present invention. All such modifications are intended to be within the scope of the claims appended hereto.

What is claimed is:

1. An in vitro method of identifying an agent that modulates a deacetylase activity of a human mitochondrial NAD-dependent deacetylase SIRT3 polypeptide, the method comprising:
   contacting an enzymatically active mitochondrial NAD-dependent deacetylase polypeptide with a test agent in an assay mixture that comprises NAD and an acetylated histone peptide; and
   determining the effect, if any, of the test agent on the deacetylase activity of the mitochondrial NAD-dependent deacetylase SIRT3 polypeptide.

2. The method of claim 1, wherein the human mitochondrial NAD-dependent deacetylase polypeptide comprises an amino acid sequence as set forth in SEQ ID NO:1.

3. The method of claim 1, wherein the acetylated histone peptide comprises amino acids 1-22 of histone 4.

4. The method of claim 1, wherein the acetylated histone peptide contains a $^{14}$C-labeled acetyl group, and determining the effect of the agent on the deacetylase activity of the deacetylase is performed by measuring release of the radioactive acetyl group.

5. The method of claim 1, wherein determining the effect of the agent on the deacetylase activity of the deacetylase is performed by detecting binding of an antibody specific for acetylated histone.

6. The method of claim 1, wherein the acetylated histone peptide comprises an amino acid sequence selected from MSGRG(acetylated lysine)GG(acetylated lysine)GLG(acetylated lysine)GGA(acetylated lysine)RHRKV (SEQ ID NO:2), MSGRG(acetylated lysine)GG(acetylated lysine)GLG(acetylated lysine)GGA(acetylated lysine)RHRKVL-RDNIQGI (SEQ ID NO:3), and MART(acetylated lysine)QTAR(acetylated lysine)STGG(acetylated lysine)APR(acetylated lysine)QLATKAARKSA (SEQ ID NO:4).

7. The method of claim 1, wherein the acetylated histone peptide is present in the assay mixture at a concentration of from about 20 μM to about 1 mM.

8. The method of claim 1, wherein the deacetylase polypeptide is a catalytically active 28 kDa form of the deacetylase polypeptide.

9. The method of claim 1, wherein the deacetylase polypeptide lacks from about 1 to about 120 N-terminal amino acids of full-length deacetylase polypeptide.

10. The method of claim 1, wherein the deacetylase polypeptide lacks amino acids 1-100 of full-length deacetylase polypeptide.

11. The method of claim 1, wherein the deacetylase polypeptide is a fusion protein.

12. The method of claim 11, wherein the deacetylase polypeptide comprises an epitope tag.

* * * * *